United States Patent [19]
Devlin et al.

[11] Patent Number: 6,103,446
[45] Date of Patent: Aug. 15, 2000

[54] FLUORESCENT CHROMOPHORE, COVALENTLY LINKED TO AN ORGANIC SUPPORT MATERIAL

[75] Inventors: Brian Gerrard Devlin, Takarazuka; Junji Otani, Kobe; Kazuhiko Kunimoto, Takatsuki, all of Japan

[73] Assignee: Ciba Specialty Chemicals Corporation, Tarrytown, N.Y.

[21] Appl. No.: 09/017,869

[22] Filed: Feb. 3, 1998

[30] Foreign Application Priority Data

| Feb. 3, 1997 | [EP] | European Pat. Off. | 97810049 |
| Feb. 3, 1997 | [EP] | European Pat. Off. | 97810050 |
| Feb. 3, 1997 | [EP] | European Pat. Off. | 97810051 |
| Feb. 4, 1997 | [EP] | European Pat. Off. | 97810054 |
| Feb. 4, 1997 | [EP] | European Pat. Off. | 97810055 |

[51] Int. Cl.$^7$ .................. G03C 1/72; G03C 1/73
[52] U.S. Cl. .................. 430/270.1; 430/288.1; 430/286.1; 430/281.1
[58] Field of Search .................. 430/270.1, 933, 430/281.1, 288.1, 286.1, 139; 526/259

[56] References Cited

U.S. PATENT DOCUMENTS

| 4,728,724 | 3/1988 | Jones, Jr. et al. | 430/19 |
| 5,047,444 | 9/1991 | DeVoe et al. | 522/99 |
| 5,244,994 | 9/1993 | Linehan | 526/259 |
| 5,665,857 | 9/1997 | Shi | 528/373 |
| 5,856,508 | 1/1999 | Jaffe et al. | 548/301.7 |

FOREIGN PATENT DOCUMENTS

| 0456609 | 11/1991 | European Pat. Off. . |
| 2292947 | 3/1996 | United Kingdom . |
| 9415441 | 7/1994 | WIPO . |

OTHER PUBLICATIONS

Harris et al, ACS Symp. Ser. 132 (1980) pp. 39–45.
Chemistry Letters, pp. 1149–1152, (1989).
Adv. Mater. (1991), No. 12, pp. 605–608.

*Primary Examiner*—Janet Baxter
*Assistant Examiner*—Yvette M. Clarke
*Attorney, Agent, or Firm*—Kevin T. Mansfield; David R. Crichton

[57] ABSTRACT

A composition comprising a solid organic support material to which are either directly, or via a bridging group, covalently linked fluorescent chromophores, characterized in that the chromophores are selected from the group consisting of benzo[4,5]imidazo[2,1-a]isoindol-11-ones.

12 Claims, No Drawings

FLUORESCENT CHROMOPHORE, COVALENTLY LINKED TO AN ORGANIC SUPPORT MATERIAL

The instant invention relates to a composition comprising a solid organic support material to which are either directly, or via a bridging group, covalently linked fluorescent chromophores, characterized in that the chromophores are selected from the group consisting of benzo[4,5]imidazo[2,1-a]isoindol-11-ones.

Further, the present invention concerns a process for the preparation of the inventive composition and its use as fluorescent material.

Over many years the concept of preparing fluorescent materials by covalently attaching a fluorescent moieties to a polymer backbone is one that has been studied by a number of scientists. For example, Y. Morishima et.al. (Chemistry Letters pp 1149, 1989) covalently attached rhodamine B moieties to a polymer backbone, whilst H-U. Siegmund (Ad. Mater. 3(12), 605 (1991)) successfully attached coumarin type structures to a polymer. In all cases the fluorescent moiety attached can be classified as a dye molecule. Typically, dye molecules in the condensed state possess only little or no fluorescence at all. It is only upon dilution, preferably to the molecular state, when the material impart or display increased fluorescence. The phenomena of a molecule losing fluorescence in the condensed state is termed concentration quenching, and has been widely documented in the literature.

Correspondingly, if one prepares polymers with large weight percentage of a fluorescent moiety attached, there will come a point where the material ceases to fluoresce or only possess weak fluorescence.

F. W. Harris et.al. (ACS Symp. Ser. 132, 39 (1980)) prepared the compound 1,2,3,4-tetraphenyl-benzo[4,5]imidazo[2,1-a]isoindol-11-one as a model material for their investigations into phenylated polyimidazopyrrolones, for potential use in aerospace applications. However, in their paper they made no reference to its fluorescence behavior and gave no hints to the possibility of preparing the derivatives herein described, that could be readily polymerized and impart photo stability.

The solid-state fluorescent compound 1,2,3,4-tetrachloro-benzo[4,5]imidazo[2,1-a]isoindol-11-one, and its derivatives, are disclosed in EP-A 456 609. The (insoluble) pigments are bright yellow in color, which impart intense solid-state fluorescence and display unprecedented photostabilies for a fluorescent material.

Hence, the object of the present invention was to provide a composition with excellent solid-state fluorescence and practical solubilities on the base of derivatives of benzo[4,5]imidazo[2,1-a]isoindol-11-ones, preferably tetraphenyl derivatives thereof, which are covalently linked to a solid organic support material. Particularly, novel soluble molecules and monomers that readily facilitate themselves to undergo fluorescent composition forming reaction should be provided. Further, another object was to provide homo- and copolymers which possess high weight percent ratios of the corresponding monomer unit, carrying the chromophore, without compromising the fluorescent intensity, that is no or only a negligible loss in fluorescence intensity with increasing the weight concentration of chromophore moiety on the polymer should be obtained.

Further objects were to provide a composition where
a) an intense solution and solid-state (non-crystalline) fluorescence is present in the visible region,
b) very excellent photostabilities can be achieved,
c) high thermal stabilities are achieved,
d) soluble and insoluble fluorescent compositions can be generated,
e) migration of the fluorescent molecules is essentially excluded,
f) a high lightfastness is achieved, and
g) an easy preparation for the materials, like single pot reactions is possible.

Accordingly, a composition comprising a solid organic support material to which are either directly, or via a bridging group, covalently linked fluorescent chromophores, characterized in that the chromophores are selected from the group consisting of benzo[4,5]imidazo[2,1-a]isoindol-11-ones was found.

In addition, a process for the preparation of the inventive composition and its use as fluorescent material were found, too. Therefore, the first embodiment of the present relates to a composition comprising a solid organic support material to which are either directly, or via a bridging group, covalently linked fluorescent chromophores, characterized in that the chromophores are selected from the group consisting of benzo[4,5]imidazo[2,1-a]isoindol-11-ones.

In a preferred embodiment of the present invention the support material is selected from the group consisting of linear or crosslinked polymers with the pendent chromophores, and surface modified polymers containing pendent chromophores on their surfaces.

A further preferred embodiment of the present invention concerns a completion form (A), namely polymers with chromophore molecules, which are either directly or via a bridging group covalently linked to the polymer backbone.

A further preferred embodiment of the present invention concerns a completion form (B), namely organic support materials to which chromophore molecules are either directly, or via a bridging group, covalently linked on the surface of the said support materials.

The following description relates to completion form (B), which as compared to the completion form (A) possesses the further advantage of reducing the consumption of chromophore molecules, arising from the fact that the chromophore molecules are not located in the interior of a polymer particle.

When applying completion form (B), the organic support material can be opaque, translucent or transparent, preferably transparent. Suitable support materials are for example thermosetting, thermoplastic or structurally crosslinked plastics. The support materials contain functional groups on the surface for the linking of the chromophore molecules. The surface groups may be obtained by a plasma treatment in a reactive gaseous atmosphere. Preferred support materials are glasses and plastics, for example plastics with functional groups.

The functional groups of the organic support material are preferably selected from the group consisting of amino-, hydroxyl-, thiol-, carboxyl-, $SO_3H$-groups or isocyanate groups. The organic support material may be a polymer that has had its surface modified, for example by plasma treatment, or it may be a natural or synthetic polymer prepared from monomers containing functional groups. Synthetic polymers may also be emulsion polymers and latices comprising at least one monomer having functional groups. Examples for natural polymers are polysaccharides like cellulose, starch or chitosane, which may be partially etherified by $C_1$–$C_4$alkyl or esterified with $C_1$–$C_8$-acyl. Synthetic polymers with functional groups are known and can be prepared by well known methods. Some examples for synthetic polymers are polyvinylalcohol and copolymers of vinyl alcohol with unsubstituted or substituted olefines as comonomers; polymethacrylic acid, polyacrylic acid and polymaleic acid and copolymers of methacrylic acid, acrylic acid and/or maleic acid with unsubstituted or substituted olefines as comonomers; polyhydroxyalkylacrylates, polyhydroxyalkylmethacrylates and polymaleic acid hydroxyalkylesters, and copolymers of hydroxyalkylesters of methacrylic acid, acrylic acid and/or maleic acid with unsubstituted or substituted olefins as comonomers; polyacrylamide and polymethacrylamide and copolymers of acryl amide, methacrylamide or both with unsubstituted or substituted olefins as comonomers; polyaminoalkylacrylates, -methacrylates and -maleic acid esters and copolymers of aminoalkylacrylates, -methacrylates, -maleic acid esters or two or three of these with unsubstituted or substituted olefins as comonomers; polyhydroxyalkyl- or polyaminoalkylvinylalcohol and copolymers of hydroxyalkylvinylether, aminoalkylvinylether or both with unsubstituted or substituted olefins as comonomers; hydroxylated polybutadienes from butadiene, isoprene or chloroprene and copolymers of butadiene, isoprene, chloroprene or two or three of these monomers with unsubstituted or substituted olefins as comonomers; hydroxy- or aminopolystyrene, chlormethylpolystyrene, and polystyrenesulfonic acid and copolymers of hydroxystyrene, aminostyrene, chloromethylstyrene, polystyrenesulfonic acid, or two or more of these monomers with unsubstituted or substituted olefins as comonomers; polyglycidyl ethers and hydroxyalkylated or aminoalkylated polyglycidyl ethers; and polyesters, polyamides and polyurethanes from hydroxyl containing monomers. The support material may also be composed of thermosetting resins, for example epoxy resins, melamine-formaldehyde resins and phenol-formaldehyde resins. Suitable olefinic comonomers are for example ethene, propene, butene, pentene, octene, vinylchloride, vinylidenechloride, styrenes and acrylonitrile. The support material may also be composed of crosslinked polymers, for example polymerisates with functionalized olefins, optionally nonfunctionalized olefinic monomers, and diolefinic monomers like butadiene, divinylbenzene or diol-diacrylates or diol-dimethacrylates, whereby the olefins may be selected from the above mentioned functional group containing olefins. Further suitable vinyl polymers are polyvinylpyrrolidone, polyvinylimidazole and polyvinylpyridine and copolymers of vinylpyrrolidone, vinylimidazole, vinylpyridine or two or three of them with unsubstituted or substituted olefins as comonomers.

The polymers may be block polymers, alternating polymers, graft polymers or random polymers.

In another preferred embodiment of this invention, the composition according to the invention is a solid-state fluorescent composition in the form of particles whereby fluorescent chromophores, selected from benzo[4,5]imidazo[2,1-a]isoindol-11-ones are covalently linked either directly or through a bridging group to the surface of the particles.

The particles may have an average diameter of 50 nm to 1000 $\mu$m, preferably 0.1 to 500 $\mu$m, more preferably 0.1 to 200 $\mu$m, most preferably 0.1 to 100 $\mu$m, and especially preferred 5 to 50 $\mu$m. The particles may be round shaped or irregularly shaped, depending on the manufacturing process, and the particles may be compact or porous.

The organic support material may for example be a shaped article from polymers, and the like. The size and shape of the article is arbitrary and depends on its final use. These shaped articles are a further object of the invention. The surface of the support material for a shaped article my be smooth or porous. The shaped articles include any composite structures.

A weight average molecular weight of the polymer of the present invention can be in the range from $10^3$ to $2\times10^6$, preferably, $10^4$ to $10^6$, more preferably, $2\times10^4$ to $10^6$, and most preferably $4\times10^4$ to $5\times10^5$ gmol$^{-1}$, as determined by gel permeation chromatography, using polystyrene standards as calibration.

The amount of chromophores is preferably from 0.00001 to 5, more preferably 0.001 to 5, more preferably 0.001 to 3, and most preferably 0.001 to 2 percent by weight, with respect to the total weight of the composition.

The fluorescent chromophore is advantageously covalently linked to the supporting material through a bridging group. The bridging group may contain 1 to 60 atoms, preferably 1 to 30 atoms, and particularly preferred 1 to 20 atoms, selected from the group consisting of C, O, S and N. The bridging group especially preferred is a hydrocarbon residue, which may be interrupted with one or more and/or end-capped with one of the heteroatoms selected from the group consisting of O, S, N or the group C(O), and which preferably contains in total from 1 to 40 atoms, more preferably 2 to 30 atoms and especially preferred 3 to 20 atoms.

The fluorescent chromophore covalently linked either directly or through a bridging group to the surface of the support material m ay be represented by formula I,

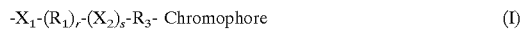

$$-X_1-(R_1)_r-(X_2)_s-R_3-\text{Chromophore} \qquad (I)$$

wherein $X_1$ and $X_2$ each independently from one another means a direct bond, or $X_1$ and $X_2$ each independently from one another mean -O-, -S-, -NR$_2$-, -C(O)-O-, -O-C(O)-, -O-C(O)-O-, -SO$_2$-O-, -O-SO$_2$-, -O-SO$_2$-O-, -NR$_2$-C(O)-, -C(O)-NR$_2$-, -NR$_2$-C(O)-O-, O-C(O)-NR$_2$-, -NR$_2$-C(O)-NR$_2$-, -NR$_2$-SO$_2$-, -SO$_2$-NR$_2$-, -NR$_2$-SO$_2$-O-, O-SO$_2$-NR$_2$- or -NR$_2$-SO$_2$-NR$_2$- each $R_1$ independently from one another means a bivalent bridging group, Chromophore stands f or the monovalent molecule, $R_2$ each independently from one another is H, $C_1$–$C_{12}$alkyl, $C_5$- or $C_6$cycloalkyl, $C_5$- or $C_6$cycloalkylmethyl or -ethyl, phenyl, benzyl or 1-phenyl-2-ethyl, $R_3$ each independently from one another are a direct bond, $C_1$–$C_{18}$alkylene, $C_5$- or $C_6$cycloalkylene, $C_6$–$C_{10}$arylene or $C_7$–$C_{12}$ aralkylene, r means the numbers 0 or 1 and s means the numbers 0 or 1, with the proviso that s is 0, if r is 0, and x means the numbers 0 or 1 and y means the numbers 0 or 1, with the proviso that y is 0, if x is 0.

In the context of alkyl, $R_2$ is preferably 1 to 6 and especially preferred 1 to 4 C-atoms. Some examples are methyl, ethyl, n- or i-propyl, butyl, pentyl, hexyl and octyl. In the context of cycloalkyl $R_2$ is preferably cyclohexyl, and in the context of cycloalkylmethyl cyclohexylmethyl in a preferred embodiment $R_2$ means H or $C_1$–$C_4$alkyl. The bivalent bridging group is preferably a hydrocarbon residue, which preferably contains 1 to 30, more preferably 2 to 20, most preferably 3 to 20 and particularly preferred 3 to 18 C-atoms, which is unsubstituted or one or more times substituted with $C_1$–$C_4$alkyl, $C_1$–$C_4$alkoxy or =O. The hydrocarbon residue may be also one or more times interrupted with heteroatoms selected from the group consisting of -O-, -S- and -NR$_2$-, whereby $R_2$ is preferably H or $C_1$–$C_4$alkyl.

The bivalent bridging group can be $C_1$–$C_{20}$-, preferably $C_2$–$C_{12}$alkylene, which may be linear or branched. Some examples are methylene, ethylene, 1,2- or 1,3-propylene, 1,2-, 1,3- or 1,4-butylene, pentylene, hexylene, octylene, dodecylene, tetradecylene, hexadecylene and octadecylene.

The bivalent bridging group can be polyoxyalkylene with 2 to 12, preferably 2 to 6 and more preferably 2 to 4 oxyalkylene units and 2 to 4, preferably 2 or 3 C-atoms in the alkylene moiety. Especially preferred is polyoxyethylene and polyoxypropylene with 2 to 6 oxyalkylene units.

The bivalent bridging group may be $C_5$–$C_{12}$, preferably $C_5$–$C_8$- and most preferably $C_5$ or $C_6$-cycloalkylene like for example cyclopentylene, cyclohexylene, cyclooctylene or cyclododecylene.

The bivalent bridging group may be $C_5$–$C_{12}$-, preferably $C_5$–$C_8$- and more preferably $C_5$- or $C_6$-cycloalkyl-$C_1$–$C_{12}$-alkylene and most preferably $C_5$- or $C_6$-cycloalkyl-$C_1$–$C_4$-alkylene. Some examples are -cyclopentyl-$C_nH_{2n}$- and -cyclohexyl-$C_nH_{2n}$-, wherein n means a number of 1 to 4. Especially preferred is -cyclohexyl-$CH_2$-.

The bivalent bridging group may be $C_5$–$C_{12}$-, preferably $C_5$–$C_8$- and more preferably $C_5$- or $C_6$-cycloalkane-($C_1$–$C_{12}$ alkylene)$_2$- and most preferably -($C_1$–$C_4$-alkylene)$_2$. Some examples are cyclopentane-($C_nH_{2n}$-)$_2$ and cyclohexane-($C_nH_{2n}$-)$_2$, wherein n means a number of 1 to 4. Especially preferred is -$CH_2$-cyclohexane-$CH_2$-.

The bivalent bridging group may be $C_6$–$C_{14}$ arylene and preferably $C_6$–$C_{10}$ arylene, for example naphthylene or more preferably phenylene. The bivalent bridging group may be $C_7$–$C_{20}$ aralkylene and preferably $C_7$–$C_{12}$ aralkylene. More preferred is arylene-$C_nH_{2n}$-, wherein arylene means naphthylene and preferably phenylene, and n means a number from 1 to 4. Examples are benzylene and phenylethylene.

The bivalent bridging group may be arene-($C_nH_{2n}$-)$_2$-, wherein arene is preferably naphthalene and more preferably benzene and n is a number from 1 to 4. Examples are xylene and benzene($CH_2CH_2$)$_2$-.

$R_3$ contains as alkylene preferably 1 to 12 and more preferably 1 to 6 C-atoms. Especially preferred examples are methylene, ethylene, 1,2- or 1,3-propylene and 1,2-, 1,3- and 1,4-butylene. $R_3$ means as arylene preferably phenylene and as aralkylene preferably benzylene.

In a preferred embodiment the bridging group may be selected from the formula Ia $$—C(O)—O—R'—O—C(O)—(R'')— \quad \text{(Ia)},$$

wherein R' is $C_2$ to $C_{20}$, preferably $C_2$ to $C_{12}$, and more preferably $C_2$ to $C_6$alkylene, phenylene, benzylene, or oligoxyalkylene with preferably 2 to 6, and more preferably 2 to 4 oxyethylene and/or oxypropylene units, and R" means a direct bond, $C_1$ to $C_{12}$alkylene, phenylene or benzylene.

The chromophores in formula I inventively are selected from the group of consisting of derivatives of benzo[4,5] imidazo[2,1-a]isoindol-11-one.

The monovalent chromophore residues in formula I may be unsubstituted or substituted with F, Cl, Br, I, -CN, -$NO_2$, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, $C_5$ to $C_{17}$ heteroaryloxy, $C_3$ to $C_{12}$ cycloalkylalkyloxy, $C_6$ to $C_{18}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{17}$ heteroaralkylthio, $C_1$ to $C_{18}$ alkyl-SO- or -$SO_2$, $C_3$ to $C_{12}$ cycloalkyl-SO- or -$SO_2$, $C_6$ to $C_{18}$ aryl-SO- or -$SO_2$, $C_5$ to $C_{17}$ heteroaryl-SO- or -$SO_2$, $C_3$ to $C_{12}$ cycloalkylalkyl-SO- or -$SO_2$, $C_6$ to $C_{18}$ aralkyl-SO- or -$SO_2$, $C_5$ to $C_{17}$ heteroaralkyl-SO- or -$SO_2$, tertiary amino with 3 to 30 carbon atoms, and alkoxyalkyl with 2 to 20 carbon atoms.

The cyclic aliphatic and aromatic residues (substituents) may be also substituted, for example with F, Cl, Br, I, -CN, -$NO_2$, $C_1$ to $C_{18}$ alkyl, $C_3$ to $C_{12}$ cycloalkyl, $C_6$ to $C_{18}$ aryl, $C_3$ to $C_{12}$ cycloalkylalkyl, $C_6$ to $C_{18}$ aralkyl, $C_5$ to $C_{17}$ heteroaralkyl, $C_1$ to $C_1$ alkyloxy, $C_3$ to $C_{12}$ cycloalkyloxy, $C_6$ to $C_{18}$ aryloxy. The substituent alkyl may be linear or branched and may be substituted with a halogen like F or Cl.

Examples of substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO-, methyl- or ethyl-$SO_2$-, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

The number of substituents is arbitrary and depends essentially upon synthetic possibilities and the desired optical properties pertaining to fluorescence and absorption.

The benzo[4,5]imidazo[2,1-a]isoindol-11-ones used in completion form (B) are preferably monovalent residues and may be selected from the formulae II and IIa,

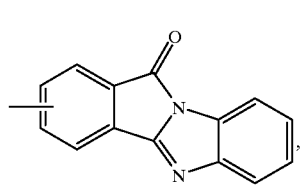

(II)

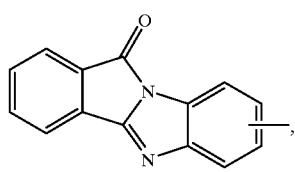

(IIa)

wherein neighboring carbon atoms of the benzene rings can be condensed with benzene rings, heteroaromatic rings or both, and to these rings can be linked to a free bond rather than benzene rings of the core polycyclic structure, moreover, the aromatic rings are unsubstituted or substituted with F, Cl or Br, I, -CN, -$NO_2$, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, $C_5$ to $C_{17}$ heteroaryloxy, $C_3$ to $C_{12}$ cycloalkylalkyloxy, $C_6$ to $C_{18}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{17}$ heteroaralkylthio, $C_1$ to $C_{18}$ alkyl-SO- or -$SO_2$, $C_3$ to $C_{12}$ cycloalkyl-SO- or -$SO_2$, $C_6$ to $C_{18}$ aryl-SO- or -$SO_2$, $C_5$ to $C_{17}$ heteroaryl-SO- or -$SO_2$, $C_3$ to $C_{12}$ cycloalkylalkyl-SO- or -$SO_2$, $C_6$ to $C_{18}$ aralkyl-SO- or -$SO_2$, $C_5$ to $C_{17}$ heteroaralkyl-SO- or -$SO_2$, tertiary amino with 3 to 30 carbon atoms, and alkoxyalkyl with 2 to 20 carbon atoms.

The cyclic aliphatic and aromatic residues may be also substituted, for example with F, Cl, Br, I, -CN, -$NO_2$, $C_1$ to $C_{18}$ alkyl, $C_3$ to $C_{12}$ cycloalkyl, $C_6$ to $C_{18}$ aryl, $C_3$ to $C_{12}$ cycloalkylalkyl, $C_6$ to $C_{18}$ aralkyl, $C_5$ to $C_{17}$ heteroaralkyl, $C_1$ to $C_1$ alkyloxy, $C_3$ to $C_{12}$ cycloalkyloxy, $C_6$ to $C_{18}$ aryloxy. The cyclic aliphatic and aromatic residues (substituents) may be also substituted, for example with halogens like F, Cl or Br; or -CN, -$NO_2$, $C_1$ to $C_{18}$ alkyl, $C_3$ to $C_{12}$ cycloalkyl, $C_6$ to $C_{18}$ aryl, , $C_3$ to $C_{12}$ cycloalkylalkyl, $C_6$ to $C_{18}$ aralkyl, $C_5$ to $C_{17}$ heteroaralkyl, $C_1$ to $C_1$ alkyloxy, $C_3$ to $C_{12}$cycloalkyloxy, $C_6$ to $C_{18}$aryloxy. The substituent alkyl may be linear or branched and may be substituted with halogen like F or Cl.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl- SO-, methyl- or ethyl-$SO_2$-, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

phenyl, benzyl, $C_1$ to $C_{12}$ alkylphenyl or $C_1$ to $C_{12}$ alkylbenzyl. $R_{05}$ in formula IIc means preferably H.

Some preferred examples of solid-state fluorescent chromophores corresponding to formula I are

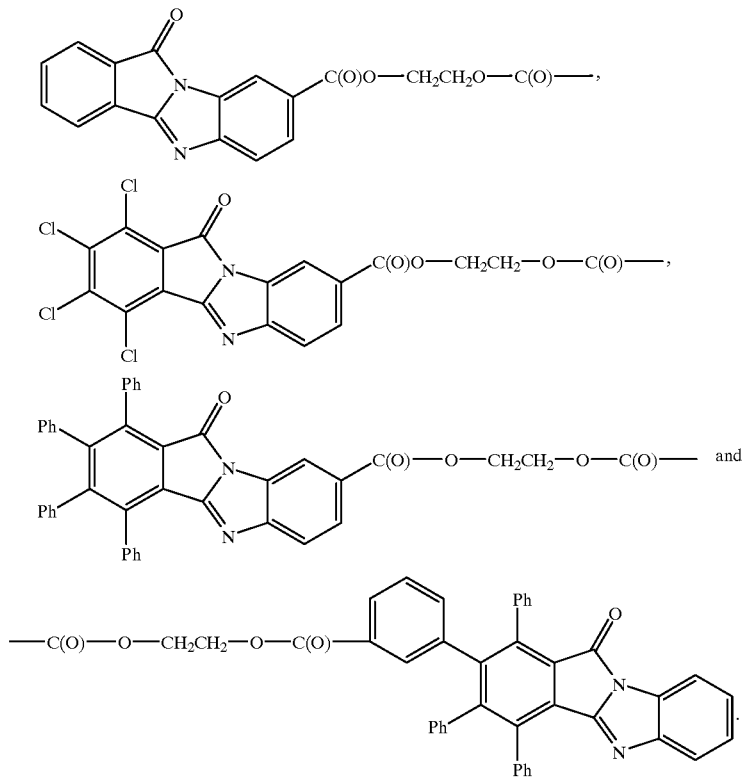

Preferably 1 or 2 rings are condensed with the neighboring carbon atoms to form bicyclic or tricyclic systems. They may be selected from benzene, furan, thiophene, pyrrole, pyridine, and pyrimidine.

In a preferred embodiment the monovalent fluorescent residues correspond to formulae IIb and IIc,

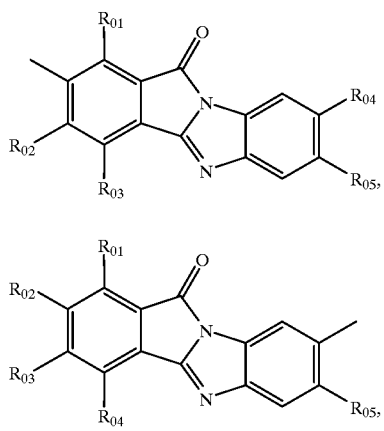

wherein $R_{01}$, $R_{02}$, $R_{03}$, $R_{04}$, and $R_{05}$ independently from one another mean H, Cl, $C_1$ to $C_{18}$ alkyl, $C_1$ to $C_{18}$ alkoxy, The composition according to completion form B may be prepared according to well known immobilization methods. A further object of the invention is a process for the preparation of the composition according to completion form B, characterized in that a organic support material, containing functional groups on the surface, is reacted with functionalized fluorescent chromophores.

The reaction may be carried-out by dissolving the functional chromophore compound in an inert solvent, adding a support material and reacting the mixture at suitable temperatures, for example 0 to 200° C. and preferably 20 to 150° C. Suitable solvents are described later. The isolation is carried-out by known filtration methods, and the material may be purified by washing, and finally it may be dried.

The immobilization and the synthesis of bridging groups can be carried out according to methods well known in the art and are well documented in the literature. In principle it is possible to covert one functional group into another functional group, for example -$CH_2OH$— groups through oxidation into carboxylic acids, carboxylic acids in amides or carboxylic acids into halogenides, amine groups into isocyanate groups, alcohols or amines into carbonates or urethanes. It is also possible, to react alcohols or amines with halogen carboxylic acids (for example monochloro acetic acid or chloromethylbenzoic acid which may then be linked to hydroxyl or amino groups). It is further possible to carry out chain extensions with di-functional agents like epoxides, azirines, diols, diamines, dicarboxylic acids or -esters and diisocyanates. Reactions using di-functional agents can be single-step or multi-step, depending on the degree of chain length desired. The bridging groups may be introduced through the functional groups of the support material or the functional groups of the chromophore molecule.

A further preferred embodiment this invention concerns completion form (A), according to which the inventive composition comprises as a support material a polymer backbone to which are either directly or via a bridging groups the fluorescent molecules are covalently linked.

The preparation of polymers and their immobilization is well known in the art. In principle there may be used two procedures. In a first aspect it is possible to polymerize monomers with pendent chromophore molecules. In a second aspect it is possible to use polymers with pendent functional groups and to react them with chromophore molecules containing functional groups.

For the fluorescent compounds, as well as the bridging groups, the accomplishments and preferred embodiments described for completion form (B) are to be considered to apply to completion form (A).

The designated fluorescent compounds are linked through functional groups bonded to structural units of the backbone. Examples of functional groups are -OH, -SH, -NH$_2$, -NHR$_2$, -CH=O, carboxylic acid, -SO$_3$H, epoxide, vinyl or isocyanate, wherein R$_2$ is preferably H or C$_1$ to C$_4$ alkyl.

The polymers can be selected from natural or synthetic polymers. Examples of natural polymers are polysaccharides like cellulose, starch or chitosane, which may be partially etherified by C$_1$–C$_4$alkyl or esterified with C$_1$–C$_8$ acyl. Synthetic polymers with functional groups can be prepared in accordance with well known methods.

Some examples of synthetic polymers are polyvinylalcohol and copolymers of vinyl alcohol with unsubstituted or substituted olefines as comonomers; polymethacrylic acid, polyacrylic acid and polymaleic acid and copolymers of methacrylic acid, acrylic acid and/or maleic acid with unsubstituted or substituted olefines as comonomers; polyhydroxyalkylacrylates, polyhydroxyalkylmethacrylates and polymaleic acid hydroxyalkylesters, and copolymers of hydroxyalkylesters of methacrylic acid, acrylic acid and/or maleic acid with unsubstituted or substituted olefins as comonomers; polyacrylamide and polymethacrylamide and copolymers of acryl amide, methacrylamide or both with unsubstituted or substituted olefins as comonomers; polyaminoalkylacrylates, -methacrylates and -maleic acid esters and copolymers of aminoalkylacrylates, -methacrylates, -maleic acid esters or two or three of these with unsubstituted or substituted olefins as comonomers; polyhydroxyalkyl- or polyaminoalkylvinylalcohol and copolymers of hydroxyalkylvinylether, aminoalkylvinylether or both with unsubstituted or substituted olefins as comonomers; hydroxylated polybutadienes from butadiene, isoprene or chloroprene and copolymers of butadiene, isoprene, chloroprene or two or three of these monomers with unsubstituted or substituted olefins as comonomers; hydroxy- or aminopolystyrene, chlormethylpolystyrene, and polystyrenesulfonic acid and copolymers of hydroxystyrene, aminostyrene, chloromethylstyrene, polystyrenesulfonic acid, or two or more of these monomers with unsubstituted or substituted olefins as comonomers; polyglycidyl ethers and hydroxyalkylated or aminoalkylated polyglycidyl ethers; and polyesters, polyamides and polyurethanes from hydroxylic group containing monomers. The polymer may also be composed of thermosetting resins, for example epoxide resins, melamine-formaldehyde resins and phenolformaldehyde resins. Suitable olefinic comonomers are for example ethene, propene, butene, pentene, octene, vinylchloride, vinylidenechloride, styrenes and acrylonitrile.

Further suitable vinyl polymers are polyvinylpyrrolidone, polyvinylimidazole and polyvinylpyridine and copolymers of vinylpyrrolidone, vinylimidazole, vinylpyridine or two or three of them together with unsubstituted or substituted olefins as comonomers.

The polymer may also be composed of crosslinked polymers, for example polymerisates with functionalized olefins, optionally nonfunctionalized olefinic monomers, and di-olefinic monomers like butadiene, divinylbenzene or dioldiacrylates or dioldimethacrylates, whereby the olefins may be selected from the above mentioned functional group containing olefins. Particularly, thermosetting resins are preferred which are selected from the group consisting of epoxide resins, melamine-formaldehyde resins and phenolformaldehyde resins.

The weight average molecular weight of the polymer of the present invention usually is chosen in the range from $10^3$ to $2 \times 10^6$, preferably from $10^4$ to $10^6$, more preferably from $2 \times 10^4$ to $10^6$, and most preferably from $4 \times 10^4$ to $5 \times 10^5$ gmol$^{-1}$, preferably determined by gel permeation chromatography, using polystyrene standards as a calibration.

The weight ratio of chromophore structural units to non-fluorescent structural units is dependent on the actual practical application, hence there are no well defined preferred ratios, other than the broad range 100:0 to 1:999. In certain applications where both color strength and fluorescence are required, then the preferred ratios of chromophore structural units to non-fluorescent structural units are 20:80 to 100:0, preferably 50:50 to 100:0 and more preferably 80:20 to 100:0. In circumstances where fluorescence is desired but color strength is not required, then the preferred ratio of chromophore structural units to non-fluorescent structural units are 20:80 to 1:999, more preferably 10:90 to 1:999 and more preferably 5:95 to 1:999.

In one embodiment of the polymeric composition of the invention and as a further object of the invention the polymer can be in the form of particles, which may be obtained by milling polymers or by emulsion polymerizations. The particles may have an average diameter of 50 nm to 1000 μm, preferably 0.1 to 500 μm, more preferably 0.1 to 200 μm, most preferably 0.1 to 100 μm, and especially preferred 5 to 50 μm. The particles may be round shaped or irregularly shaped, depending on the manufacturing process, and the particles may be compact or porous.

The polymer may be composed from monomeric units with covalently linked monovalent and/or divalent residues of a selected chromophore (the polymer may optionally contain other co-momomeric units);

(III)

or may be composed of recurring crosslinkable units of formula IIIa alone or in combination with one or both of the structural units of formulae III and IIIa,

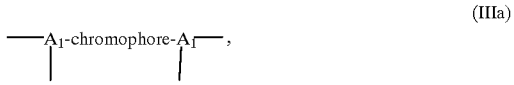

(IIIa)

wherein

A and A$_1$ are trivalent organic residues,

Chromophore means, either directly or via a bridging group, a covalently linked monovalent fluorescent chromophore defined before, whereby A is copolymerizable with $A_1$ when used in combination.

The polymer may additionally contain structural units of formula IIIa, $$—A_2—$$ (IIIb), wherein $A_2$ means the same or a different divalent residue from the same group of A.

A, $A_1$ and $A_2$ may be derived from monomers selected from the group consisting of olefins, polyalcohols (preferably diols or triols), polyamines (preferably diamines and triamines), polyisocyanates (preferably di- or tri-isocyanates), carboxylic (preferably di- or tricarboxylic acids) acids and polyepoxides (preferably di- or triepoxides).

The weight ratio of structural elements of formula III, IIIa, or IIIb, resp., to non-fluorescent structural units is dependent on the actual practical application, hence there are no well defined preferred ratios, other than the broad range 100:0 to 1:999. In certain applications where both color strength and fluorescence are required, then the preferred ratios of chromophore structural units to non-fluorescent structural units is 20:80 to 100:0, preferably 50:50 to 100:0 and more preferably 80:20 to 100:0. In circumstances where fluorescence is desired but color strength is not required, then the preferred ratio of chromophore structural units to non-fluorescent structural units is 20:80 to 1:999, more preferably 10:90 to 1:999 and more preferably 5:95 to 1:999.

In a preferred embodiment the polymers according to the invention contain recurring structural units of formula IV, recurring structural units of formula IVa, and optionally recurring structural units of formula V,

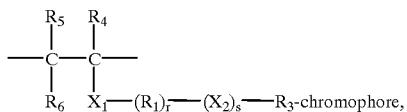

(IV)

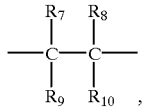

(V)

wherein $X_1$ and $X_2$ each independently of one another mean a direct bond, or $X_1$ and $X_2$ each independently of one another mean -O-, -S-, $-NR_2-$, -C(O)-O-, -O-C(O)-, -O-C(O)-O-, $-SO_2-O-$, $-O-SO_2-$, $-O-SO_2-O-$, $-NR_2-C(O)-$, $-C(O)-NR_2-$, $-NR_2-C(O)-O-$, $O-C(O)-NR_2-$, $-NR_2-C(O)-NR_2-$, $-NR_2-SO_2-$, $-SO_2-NR_2-$, $-NR_2-SO_2-O-$, $-O-SO_2-NR_2-$ or $-NR_2-SO_2-NR_2-$, $R_1$ means a bivalent bridging group, chromophore means a monovalent fluorescent moiety, $R_2$ means H, $C_1-C_{12}$ alkyl, $C_5-$ or $C_6$ cycloalkyl, $C_5-$ or $C_6$ cycloalkylmethyl or -ethyl, phenyl, benzyl or 1-phenyl-2-ethyl, $R_3$ means a direct bond, $C_1-C_{18}$ alkylene, $C_5-$ or $C_6$-cycloalkylene, $C_6-C_{10}$ arylene or $C_7-C_{12}$ aralkylene, the r each independently of one another mean the numbers 0 or 1 and the s each independently of one another mean the numbers 0 or 1, with the proviso that if s is 0, r is 0, $R_4$ and $R_5$ each independently of one another mean H, $C_1-C_6$ alkyl, $C_6-C_{10}$ aryl or $C_7-C_{12}$ aralkyl, $R_6$ means H or the group $-C(O)O-R_{11}$, $R_7$ means H, $C_1-C_6$ alkyl, $C_6-C_{10}$ aryl or $C_7-C_{12}$ aralkyl, $R_8$ means H, F, Cl, CN, $C_1-C_6$alkyl or $C_6-C_{10}$aryl, $R_9$ means H, $C_1-C_6$alkyl or $-C(O)O-R_{11}$, $R_{10}$ means H, $C_1-C_6$ alkyl, $C_6-C_{10}$ aryl, $C_7-C_{12}$ aralkyl, imidazolyl, pyrrolidonyl, F, Cl, CN or the group $-X_1-(R_1)_r-(X_2)_s$-H, and $R_{11}$ means H, K, Na, $C_1-C_{18}$ alkyl, $C_1-C_{18}$ hydroxyalkyl, cyclohexyl, cyclopentyl, cyclohexylmethyl, phenyl, $C_1-C_4$alkylphenyl, benzyl or $C_1-C_4$ alkylbenzyl.

For $X_1$, $X_2$, $R_1$, $R_2$, $R_3$, r, s, and Chromophore the meanings and preferred embodiments as described for completion form (B) also pertain to completion form (A).

$R_4$ and $R_5$ mean as alkyl preferably $C_1-C_4$ alkyl, for example methyl, ethyl, n- or i-propyl and n-, i- or t-butyl, as aryl preferably naphthyl or phenyl, and as aralkyl preferably benzyl. Especially preferred $R_4$ is H and $R_5$ is H or methyl.

$R_6$ means preferably H, -C(O)OH or $-C(O)O-C_1$ to $C_4$-alkyl.

$R_7$ means as alkyl preferably $C_1$ to $C_4$alkyl, for example methyl, ethyl, n- or i-propyl, and n-, i- or t-butyl; as aryl preferably naphthyl or phenyl and as aralkyl preferably benzyl. Especially preferred $R_7$ is H.

$R_8$ for alkyl means is preferably $C_1$ to $C_4$alkyl, for example methyl, ethyl, n- or i-propyl and n-, i- or t-butyl, and for aryl it is preferably phenyl or naphthyl. Especially preferred $R_8$ is H, Cl, CN, phenyl or $C_1$ to $C_4$ alkyl.

$R_9$ means as alkyl preferably $C_1-C_4$ alkyl, for example methyl, ethyl, n- or i-propyl and n-, i- or t-butyl. In the group $-C(O)O-R_{11}$, $R_{11}$ means preferably H or $C_1-C_{12}$ alkyl, more preferably $C_1-C_6$ alkyl, like for example methyl, ethyl, propyl, butyl, pentyl, hexyl, heptyl, octyl, nonyl, decyl, undecyl, dodecyl, tetradecyl, hexadecyl and octadecyl. Especially preferred $R_9$ is H, -C(O)OH or $-C(O)-O-C_1-C_4$alkyl.

$R_{10}$ means as alkyl preferably $C_1-C_4$alkyl, for example methyl, ethyl, n- or i-propyl and n-, i- or t-butyl, as aryl preferably phenyl and naphthyl, and as aralkyl preferably benzyl. $R_{10}$ means preferably H, $C_1-C_4$ alkyl, phenyl, pyrrolidonyl, F, Cl, CN or the group $-X_1-(R_1)_r-(X_2)_s$-H.

$R_{11}$ may be for example H, K, Na, $C_1-C_6$alkyl, $C_1-C_6$-hydroxyalkyl, cyclohexyl, cyclopentyl, cyclohexylmethyl, phenyl, methylphenyl, benzyl or methylbenzyl.

The weight ratio of structural elements of formula IV to non-fluorescent structural units is dependent on the actual practical application, hence there are no well defined preferred ratios, other than the broad range 100:0 to 1:999. In certain applications where both color strength and fluorescence are required, then the preferred ratios of chromophore structural units to non-fluorescent structural units is 20:80 to 100:0, preferably 50:50 to 100:0 and more preferably 80:20 to 100:0. In circumstances where fluorescence is desired but color strength is not required, then the preferred ratio of chromophore structural units to non-fluorescent structural units is 20:80 to 1:999, more preferably 10:90 to 1:999 and more preferably 5:95 to 1:999.

The weight ratio of structural elements of formula V to fluorescent structural units is dependent on the actual practical application, hence there are no well defined preferred ratios, other than the broad range 0:100 to 999:1. In certain applications where both color strength and fluorescence are required, then the preferred ratios structural elements of formula V to fluorescent structural units is 20:80 to 1:999, more preferably 10:90 to 1:999 and more preferably 5:95 to 1:999. In circumstances where fluorescence is desired but color strength is not required, then the preferred ratio structural elements of formula V to fluorescent structural units is 20:80 to 100:0, preferably 50:50 to 100:0 and more preferably 80:20 to 100:0.

The polymers with the structural elements of formulae IV and optionally V may be crosslinked with multi-functional monomers, for example with 0.01 to 80 wt %, preferably 0.1 to 60 wt % of these monomers, related to the total weight of polymer. Depending upon the kind of polymer, it may be possible to use at least trifunctional carboxylic acids, isocyanates, alcohols, amines, vinyls or epoxides. It is also possible to employ polymerisates that contain at least two olefinically (ethylenically) unsaturated groups containing organic compounds. A wider range of crosslinking agents are well known to those familiar in the art. The ethylenically unsaturated crosslinking agents may be selected from the group consisting of divinylbenzol, bi-dimethylmaleinimid-alkylene bi-(dimethylmaleinimidyle)-methylene or -ethylene, acrylic acid- or methacrylic acid esters or -amides of polyols, preferably diols to tetrols, or polyamines respectively, preferably diamines to tetramines. Preferred crosslinking agents are selected from the group of aliphatic, cycloaliphatic and cycloaliphatic-aliphatic diols and diamines containing especially preferred 2 to 12, and particularly preferred 2 to 8 C-atoms. Some examples of these diols are alkylenediols like ethylenglycol, 1,2- or 1,3-propanediol, 1,2-, 1,3- and 1,4-butanediol, pentanediol, hexanediol, octanediol, decanediol, dodecanediol, cyclohexanediol, di(hydroxymethyl)-cyclohexane, polyoxy-alkylendiols from preferably $C_2$–$C_6$ alkylendiols with preferably 2 to 100 alkylenediol units, more preferably 2 to 50 alkylenediol units, and most preferably 2 to 20 alkylenediol units, like for example polyethylenediols, polypolypropylenediols, polybutylenediols and polyethylenepolypropylenediols, further 1,1,1-trihydroxymethylethane or -propane, pentaerythrite and dipentaerythrite. Some examples for polyamines are ethylenediamine, 1,3- and 1,3-propanediamine, 1,2-, 1,3- and 1,4-butanediamine, 1,6-hexanediamine, diethylenetriamine, triethylenetetramine, cyclohexanediamine, aminomethylcyclohexaneamine, isophorondiamine and di(aminomethyl)cyclohexane.

In a preferred embodiment of the invention the polymers contain structural elements of the formula VI,

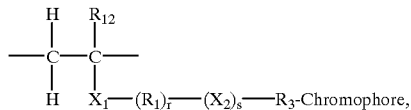
(VI)

wherein $R_{12}$ is H or methyl, and $X_1$, $X_2$, $R_1$, $R_3$, chromophore, r and s have the meanings given before, inclusive of the preferred embodiments; and optionally structural elements of formula V.

The group -$X_1$-($R_1$)$_r$-($X_2$)$_s$-$R_3$- in the structural elements of formulae VI and VIa mean preferably -C(O)-O-, -C(O)-O-$C_1$–$C_6$alkylene-O- C(O)-, -C(O)-O-($C_2$–$C_6$alkylene-O)$_u$-C(O)- with u being a number of 2 to 10, phenylene or benzylene, -C(O)-$C_6H_5$-$CH_2$- or -C(O)-$C_1$ to $C_{12}$alkylene.

The polymers with the structural elements of formulae IV or VI, and optionally structural elements of formula V may contain additionally equal or different structural elements of formula VII,

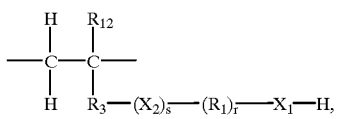
(VII)

wherein $R_{12}$, $X_1$, $X_2$, $R_1$, $R_3$, r and s have the meanings given before, inclusive of the preferred embodiments. These structural elements are preferably present when the chromophore group is introduced to the polymer through reaction between pendant functional groups on the polymer and functional groups on the respective chromophore molecules.

The polymers with the structural elements of formulae IV or VI, and optionally structural elements of formula V, contain preferably equal or different structural elements of formula VIII as preferred units of formula V,

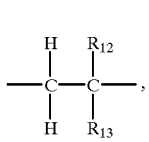
(VIII)

wherein
$R_{12}$ means H or methyl, and
$R_{13}$ means H, $C_1$–$C_4$alkyl, $C_1$–$C_4$alkoxy, -CN, Cl, phenyl, pyrrolidonyl, pyridinyl, imidazolyl, -C(O)O$R_{14}$ or -C(O)-N$R_{15}R_{16}$,
$R_{39}$ means H or $C_1$–$C_{18}$- and preferably $C_1$–$C_{12}$ alkyl, and
$R_{15}$ and $R_{16}$ independently of one another mean H or $C_1$–$C_{12}$-, and preferably $C_1$–$C_6$alkyl.

The polymers with the structural elements of formulae IV and IVa, or VI and VIa, and optionally equal or different structural elements of formula V or formula VIII, may of agents additionally contain structural elements of formulae IX or X as preferred crosslinking,

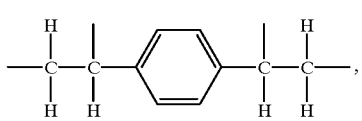
(IX)

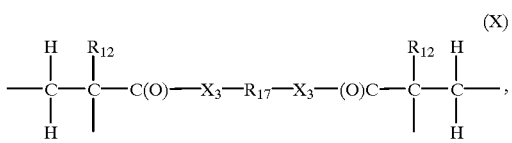
(X)

wherein
$R_{12}$ means H or methyl,
$X_3$ means -O-, -NH- or -N($C_1$–$C_4$-alkyl)-, and
$R_{17}$ means $C_2$–$C_{12}$- and preferably $C_1$–$C_6$ alkylene, cyclohexylene, cyclohexanedimethylene, phenylene, or $X_3$ means -O- and $R_{17}$ means $C_2$–$C_6$ alkylene-($C_2$–$C_6$ alkylen-O)$_{2 \ to \ 20}$- $C_2$–$C_6$ alkylene.

The polymerisates and preferred polymerisates described before may contain additionally equal or different ionic structural elements, for example of formula XI,

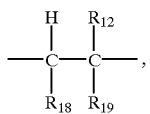

(XI)

wherein $R_{12}$ means H or methyl, $R_{18}$ means H and $R_{19}$ means $-C(O)OR_{20}$, $-SO_3R_{20}$, $-C_6H_4-COOR_{20}$, $-C_6H_4-SO_3R_{20}$, $-C_6H_4-R_{21}$ or $-C(O)-X_4-C_2-C_6$ alkylene-$R_{22}$, X4 means -O- or -NH-, $R_{18}$ and $R_{19}$ mean independently of one another $-C(O)OR_{20}$ or $-C(O)-X_4-C_2-C_6$alkylene-$R_{22}$, $R_{20}$ means an alkaline metal, preferably Li, Na or K, $R_{21}$ means an ammonium group or an ammoniummethyl group, and $R_{22}$ means an ammonium group.

The ammonium group or the ammonium in the ammoniummethyl group may be derived from primary, secondary or tertiary amine groups; preferred are quaternary ammonium groups. The ammonium groups or the ammonium in the ammoniummethyl group may correspond to the formula XII, $-^+NR_{23}R_{24}R_{25}$ (XII), wherein $R_{23}$, $R_{24}$ and $R_{25}$ are independently from one another H, $C_1-C_{18}$-, preferably $C_1-C_{12}$- and more preferably $C_1-C_6$ alkyl, $C_5$- or $C_6$cycloalkyl, phenyl, benzyl, 1-phenyl-eth-2-yl, or $R_{23}$ and $R_{24}$ together are tetramethylene, pentamethylene or $-CH_2CH_2-O-CH_2CH_2-$ and $R_{26}$ has the meaning given before.

Suitable counter anions may be derived from inorganic or organic acids, for example carboxylic acids, sulfonic acids and halogenhydrogen acids. Preferred counter anions are chloride and bromide.

The polymerisates and preferred polymerisates described before may contain additionally structural elements with acidic groups like for example -C(O)OH or -SO$_3$H, especially when emulsion polymerisates are involved.

The structural elements with acidic groups may correspond to the formula XIII,

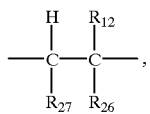

(XIII)

wherein $R_{12}$ means H or methyl, $R_{27}$ means H and $R_{26}$ means -C(O)OH, -SO$_3$H, -C$_6$H$_4$-COOH, -C$_6$H$_4$-SO$_3$H, or $R_{26}$ and $R_{27}$ means -C(O)OH.

Polymers with amino or acidic groups may be preferably soluble in water or they may be prepared by emulsion polymerization for dispersing and/or dissolving monomers.

In another preferred embodiment the polymers according to the invention may be crosslinked with difunctional molecules. These polymers may contain recurring structural elements of formula XIV alone or together with structural elements of formula IV,

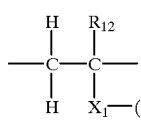 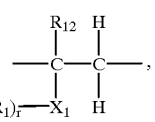

(XIV)

wherein $R_1$, $R_3$, $R_{12}$, $X_1$, $X_2$, r, s, chromophore have the meanings given before, inclusive preferred embodiments.

The weight ratio of structural elements of formula (XIV) to non-fluorescent structural units is dependent on the actual practical application, hence there are no well defined preferred ratios, other than the broad range 100:0 to 1:999. In certain applications where both color strength and fluorescence are required, then the preferred ratios of chromophore structural units to non-fluorescent structural units is 20:80 to 100:0, preferably 50:50 to 100:0 and more preferably 80:20 to 100:0. In circumstances where fluorescence is desired but color strength is not required, then the preferred ratio of chromophore structural units to non-fluorescent structural units is 20:80 to 1:999, more preferably 10:90 to 1:999 and more preferably 5:95 to 1:999.

The above crosslinked polymers with one or both structural elements of formulae XIV may contain structural elements of formulae IV, V, VIII, IX, X, XI, XII and XIII alone or in any combination of at least 2 of these structural elements, or may contain structural elements of preferred residues formulae V, IX and VIII, and further IX, X, XI, XII and XIII alone or in any combination of at least 2 of these structural elements.

Preferred divalent residues of the chromophore correspond to the formula XV,

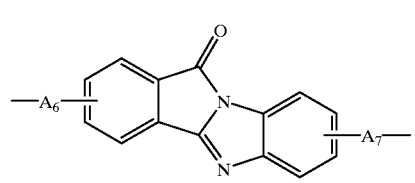

(XV)

wherein neighboring carbon atoms of the benzene rings can be condensed with benzene rings, heteroaromatic rings or both, and to these rings can be linked free bonds instead of the benzene rings of a polycyclic structure, and the aromatic rings are unsubstituted or substituted with halogen like F, Cl or Br, -CN, -NO$_2$, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, $C_5$ to $C_{17}$ heteroaryloxy, $C_3$ to $C_{12}$ cycloalkylalkyloxy, $C_6$ to $C_{18}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{17}$ heteroaralkylthio, $C_1$ to $C_{18}$ alkyl-SO- or -$SO_2$, $C_3$ to $C_{12}$ cycloalkyl-SO- or -$SO_2$, $C_6$ to $C_{18}$ aryl-SO- or -$SO_2$, $C_5$ to $C_{17}$ heteroaryl-SO- or -$SO_2$, $C_3$ to $C_{12}$ cycloalkylalkyl-SO- or -$SO_2$, $C_6$ to $C_{18}$ aralkyl-SO- or -$SO_2$, $C_5$ to $C_{17}$ heteroaralkyl-SO- or -$SO_2$, tertiary amino with 3 to 30 carbon atoms, and alkoxalkyl with 2 to 20 carbon atoms. The cyclic aliphatic and aromatic residues may be also be substituted, for example with halogens like F, Cl or Br; or -CN, -$NO_2$, $C_1$ to $C_{18}$ alkyl, $C_3$ to $C_{12}$cycloalkyl, $C_6$ to $C_{18}$ aryl, , $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, and $A_6$ and $A_7$ mean a direct bond divalent organic group.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO-, methyl- or ethyl-$SO_2$-, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

Preferably 1 or 2 rings are condensed with the neighboring carbon atoms to form bicyclic or tricyclic systems. They may be selected from benzene, furane, thiophene, pyrrole, pyridine, and pyrimidine.

In a preferred embodiment, $A_6$ and $A_7$ correspond to the formula XVI, $$-X_1-(R_1)_r-(X_2)_s-R_3- \quad (XVI),$$

wherein $X_1$, $X_2$, $R_1$, $R_3$, r and s have the meanings as described before, inclusive of the preferred embodiments.

In a preferred embodiment the bivalent chromophore residues correspond to formulae XVII and XVIIa,

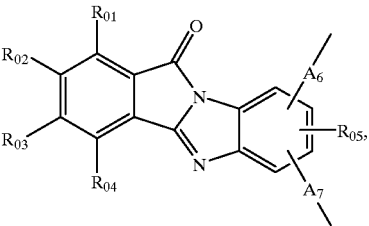

(XVII)

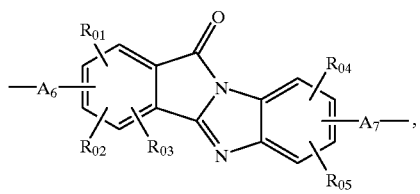

(XVIIa)

wherein $R_{01}$, $R_{02}$, $R_{03}$, $R_{04}$, and $R_{05}$ independently from one another mean H, Cl, $C_1$ to $C_{18}$ alkyl, $C_1$ to $C_{18}$ alkoxy, phenyl, benzyl, $C_1$ to $C_{12}$ alkylphenyl or $C_1$ to $C_{12}$ alkylbenzyl. $R_{05}$ means preferably H, and $A_6$ and $A_7$ correspond to a bivalent residue of formula XVI.

In a preferred embodiment the groups $A_6$ and $A_7$ may be selected from the formulae -C(O)-O-R'-O-C(O)-(R")$_u$- and -C(O)-NH-R'-NH-C(O)-(R")$_u$-, wherein R' is $C_2$ to $C_{20}$, preferably $C_2$ to $C_{12}$, and more preferably $C_2$ to $C_6$alkylene, phenylene, benzylene, or oligoxyalkylene with preferably 2 to 6, and more preferably 2 to 4 oxyethylene and/or oxypropylene units, R" means $C_1$ to $C_{12}$alkylene, phenylene or benzylene, and u means 0 or 1.

Some preferred examples of chromophore residues corresponding to formula XV are

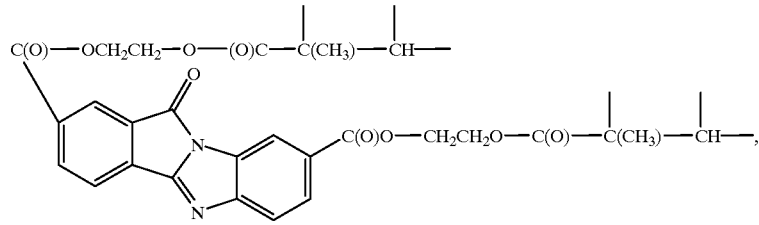

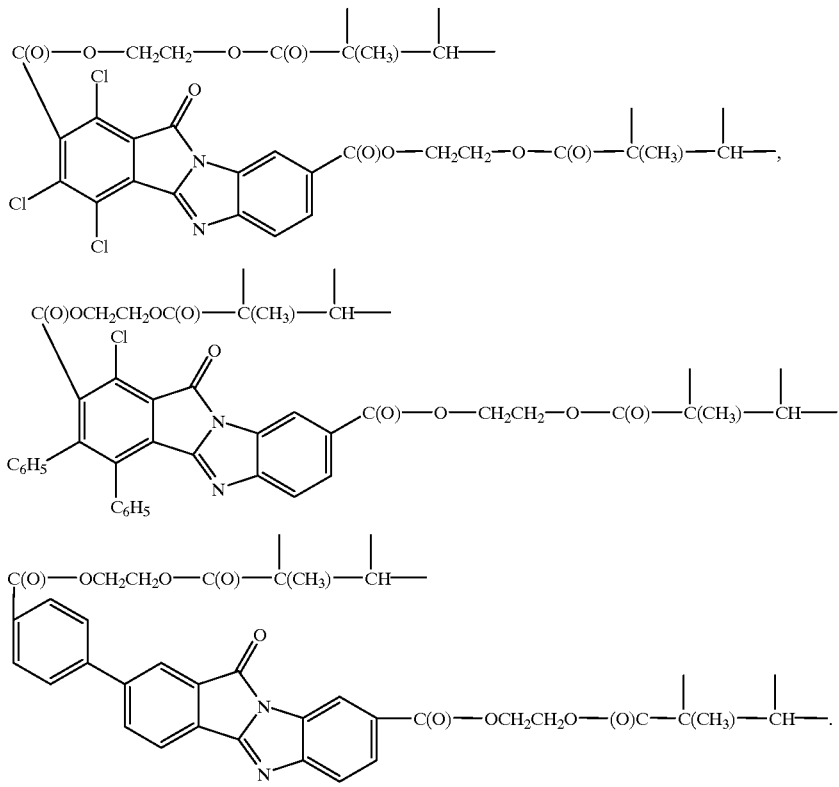

In another preferred embodiment of the invention the polymer according to the invention may contain or may be composed of functional chromophore monomers which contain two or three functional groups covalently linked via a bridging group to one ring of the chromophore core structure. Thus the polymers with recurring structural units of the formulae III, IIIa and IIIb may additionally contain, or the units of the formula IIIb may be replaced by recurring crosslinking units of the formula IIIc, IIId or both,

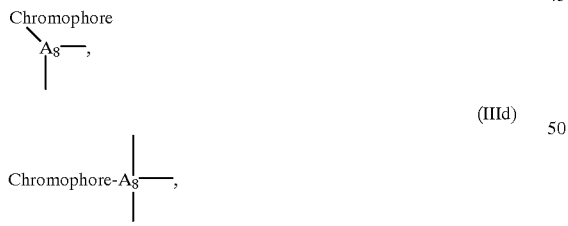

wherein $A_8$ means a trivalent or tetravalent organic residue, copolymerisable with the groups A to $A_2$, and Chromophore means a monovalent fluorescent chromophore, as defined before.

Preferred divalent and trivalent residues of the chromophore may also correspond to the formulae XX and XXa,

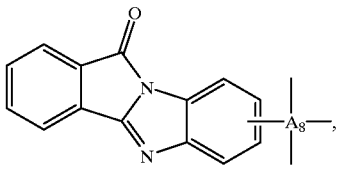

wherein neighboring carbon atoms of the benzene ring can be condensed with benzene rings, heteroaromatic rings or both, and the aromatic rings are unsubstituted or substituted with halogens like F, Cl or Br, -CN, -$NO_2$, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, $C_5$ to $C_{17}$ heteroaryloxy, $C_3$ to $C_{12}$ cycloalkylalkyloxy, $C_6$ to $C_{18}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{17}$ heteroaralkylthio, $C_1$ to $C_{18}$ alkyl-SO- or -$SO_2$, $C_3$ to $C_{12}$ cycloalkyl-SO- or -$SO_2$, $C_6$ to $C_{18}$ aryl-SO- or -$SO_2$, $C_5$ to $C_{17}$ heteroaryl-SO- or -$SO_2$, $C_3$ to $C_{12}$ cycloalkylalkyl-SO- or -$SO_2$, $C_6$ to $C_{18}$ aralkyl-SO- or -$SO_2$, $C_5$ to $C_{17}$ heteroaralkyl-SO- or -SO$_2$, tertiary amino with 3 to 30 carbon atoms, and alkoxyalkyl with 2 to 20 carbon atoms, the cyclic aliphatic and aromatic residues (substituents) may also be substituted, for example with halogens like F, Cl or Br; or -CN, -NO$_2$, C$_1$ to C$_{18}$ alkyl, C$_3$ to C$_{12}$cycloalkyl, C$_6$ to C$_{18}$ aryl, C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$ aryloxy, and A$_8$ mean a trivalent or tetravalent organic group.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO-, methyl- or ethyl-SO$_2$-, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

Preferably 1 ring is condensed with the neighboring carbon atoms to form bicyclic systems. They may be selected from benzene, furane, thiophene, pyrrole, pyridine, and pyrimidine.

In a preferred embodiment, A$_8$ corresponds to the formulae XXI or XXIa,

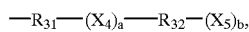
(XXI)

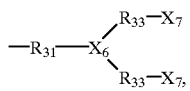
(XXIa)

wherein (a) R$_{31}$ is a direct bond, C$_1$ to C$_{12}$ alkylene, phenylene or benzylene;

X$_4$ is N, O, S, C(O)O or C(O)N;

R$_{32}$ means C$_2$ to C$_{12}$ alkyltriyl, phenyltriyl or benztriyl, when a is 1 and b is 2, or means C$_2$ to C$_{12}$ alkyltetrayl, phenyltetrayl or benztetrayl, when a is 1 and b is 3;

X$_5$ means O, S, NH, C(O)O, C(O)NH,

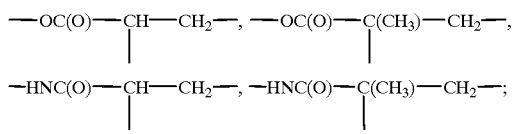

or (b) R32 is a bond, a is 0 and b is 2 or 3, X$_5$ has the above meanings and R$_{31}$ means C$_2$ to C$_{12}$ alkyltriyl, phenyltriyl or benztriyl, when b is 2, or means C$_2$ to C$_{12}$ alkyltetrayl, phenyltetrayl or benztetrayl, when b is 3;

(c) R$_{31}$ is a direct bond, C$_1$ to C$_{12}$ alkylene, phenylene or benzylene;

X$_6$ is N or C(O)N;

R$_{33}$ is C$_2$ to C$_{12}$ alkylene;

X$_7$ is O, S, C(O)O, C(O)NH, and

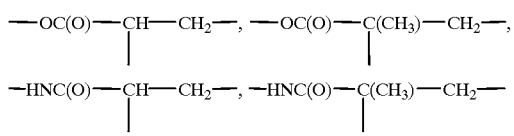

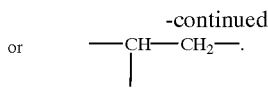

R$_{31}$ and R$_{33}$ in the meaning of alkylene contain preferably 2 to 8 and mostly preferred 2 to 4 C-atoms. R$_{32}$ in the meaning of alktriyl contain preferably 2 to 8, more preferred 2 to 6, and mostly preferred 2 to 4 C-atoms.

In a preferred embodiment the bivalent chromophore residues correspond to formulae XXII and XXIIa,

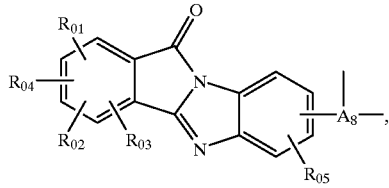
(XXII)

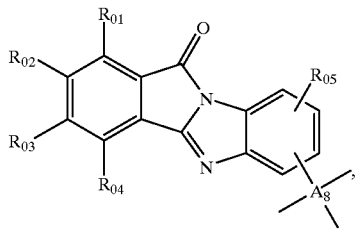
(XXIIa)

wherein

R$_{01}$, R$_{02}$, R$_{03}$, R$_{04}$, and R$_{05}$ independently from one another mean H, Cl, C$_1$ to C$_{18}$ alkyl, C$_1$ to C$_{18}$ alkoxy, phenyl, benzyl, C$_1$ to C$_{12}$ alkylphenyl or C$_1$ to C$_{12}$ alkylbenzyl, and A8 correspond to formulae XXI or XXIa. R$_{05}$ means preferably H.

In a preferred embodiment the group A$_8$ may be selected from the group

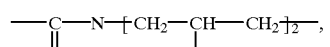

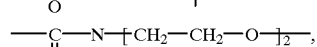

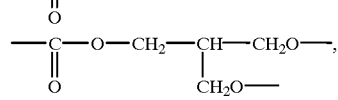

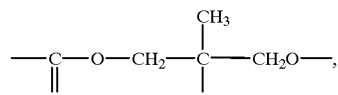

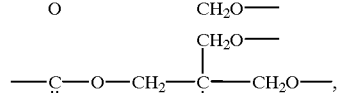

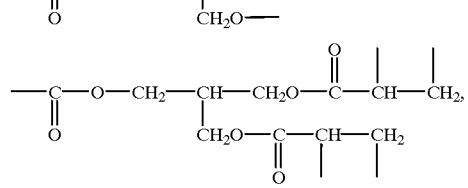

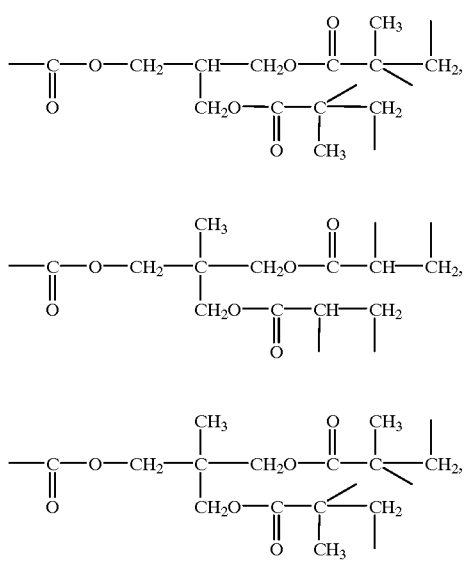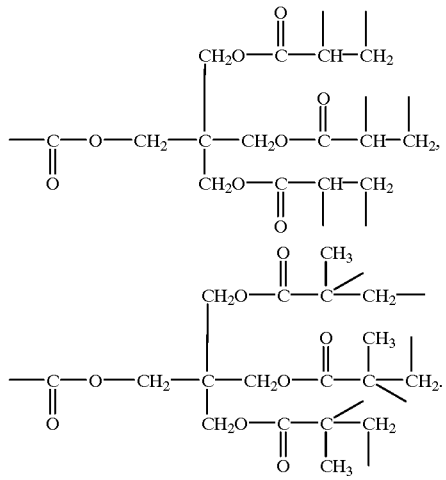
Some preferred examples are residues from the group (Ph means phenyl):
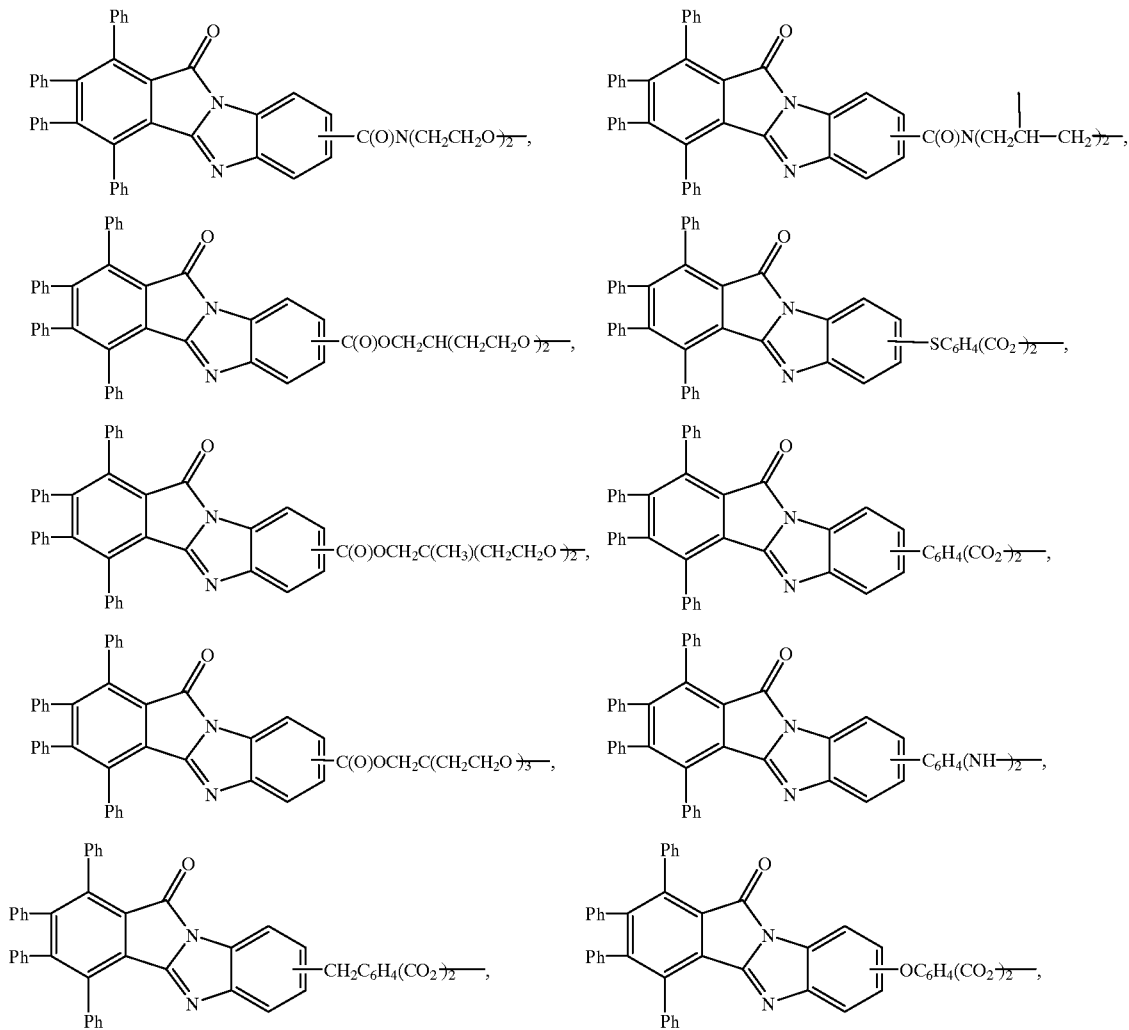

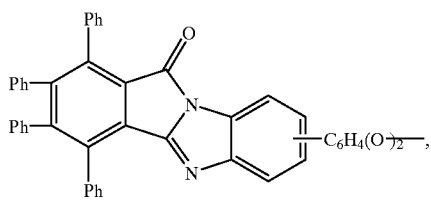
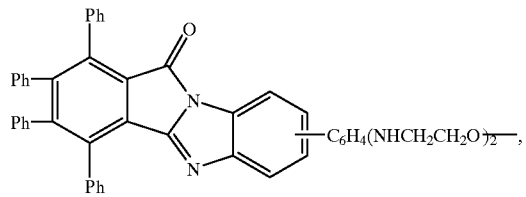
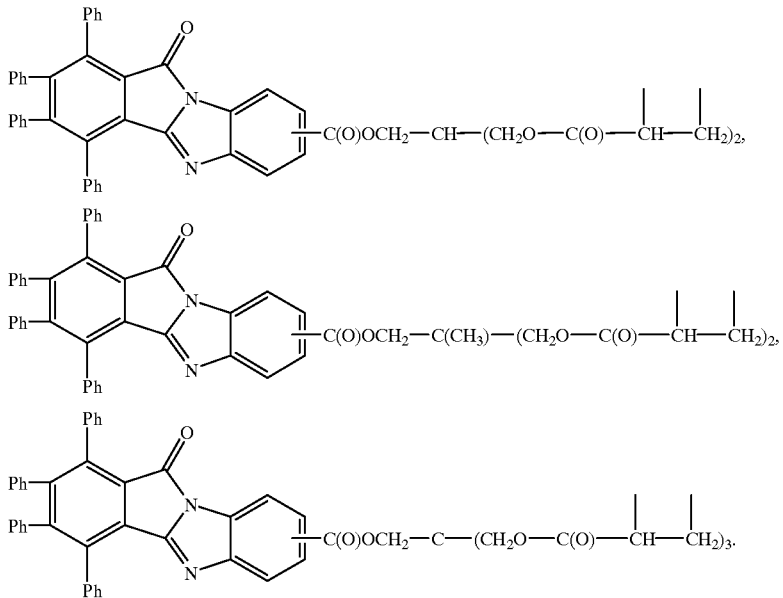

The polymers according to the invention may be random, block, graft or emulsion polymers (latices).

The preparation of polymers and their immobilization is well known in the art. In principle there may be used two procedures. In a first aspect it is possible to polymerize monomers with pendent chromophore molecules. In a second aspect it is possible to use polymers with pendent functional groups and to react them with chromophore molecules containing functional groups.

A further preferred embodiment of the invention is a process for the manufacture of the polymers according to the invention, which comprises reacting a compound of the formula XVIII, XIX, and XXIII and in any combination, alone or together with comonomers,

| | |
|---|---|
| $A'_1$—chromophore | (XVIII) |
| $A'_2$—chromophore—$A'_2$ | (XIX) |
| Chromophore-$(A'_3)_c$ | (XXIII) | wherein
$A'_1$ is a monovalent functional or polymerisable group,
$A'_2$ is a monovalent functional or polymerisable group coreactive with $A'_1$,
$A'_3$ is a monovalent functional or polymerisable group coreactive with functional or polymerisable groups on the polymer and c is 2 or 3, and Chromophore has the meaning given before, whereby the $A'_1$, $A'_2$ and $A'_3$ are linked directly or via a bridging group to the chromophore body.

A further preferred embodiment of the present invenion relates to a process for the manufacture of the inventive composition, which comprises reacting a polymer with recurring structural elements containing, either directly or through a bridging group, covalently linked functional or polymerisable groups, with a compound of the formula XVIII, XIX and/or XXIII in any chromophore combination, alone or together with comonomers,

| | |
|---|---|
| $A'_1$—Chromophore | (XVIII) |
| $A'_2$—chromophore—$A'_2$ | (XIX) |
| Chromophore-$(A'_3)_c$ | (XXIII) | wherein
$A'_1$ is a monovalent functional or polymerisable group,
$A'_2$ is a monovalent functional or polymerisable group coreactive with functional or polymerisable groups of the polymer,
$A'_3$ is a monovalent functional or polymerisable group coreactive with functional or polymerisable groups on the polymer and c is 2 or 3, and Chromophore has the meaning as given before, whereby the $A'_1$, $A'_2$ and $A'_3$ are linked directly, or via a bridging group, to the chromophore body.

The preparation of the polymers according to the invention may be carried out according to processes well known in the art of polymer chemistry for example step-growth, anionic, cationic and radical polymerisations. Known polymerization processes are solution, bulk, emulsion, photo- and interface polymerization.

Reaction temperatures may range from 0 to 250° C. The use of suitable catalysts and photoinitiators as known and not described here. However, azobisisobutyronitrile is a well known and effective radical catalyst for the thermal polymerisations of olefinically unsaturated compounds. The polymerization may be carried out by mixing the monomers, catalysts, and optionally a solvent, together and heating, irradiating or by both heating and irradiating. The polymers may be isolated by precipitation with non-solvents or removing solvents and optionally purified by repeat precipitations and drying.

The monomers are partially novel and partially known or they can be prepared by known or analogous methods.

Difunctional benzo[4,5]imidazo[2,1-a]isoindol-11-ones are novel, and in one aspect, and a further preferred embodiment of the invention, are compounds of formula XXIV,

A''$_1$—Chromophore—A''$_1$ (XXIV), wherein

A''$_1$ is a monovalent functional (also means polymerisable) group, which is linked directly or via a bridging group to the chromophore body, and Chromophore is a divalent benzo[4,5]imidazo[2,1-a]isoindol-11-one, neighboring carbon atoms of the benzene rings of the chromophore can be condensed with benzene rings, heteroaromatic rings or both, and to these rings can be linked the free bond rather than to the benzene rings of the chromophore core structure, and the aromatic rings are unsubstituted or substituted with F, Cl or Br, -CN, -NO$_2$, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_6$ to $C_{18}$ aralkyl, $C_5$ to $C_{17}$heteroaralkyl, $C_1$ to $C_{18}$alkyloxy, $C_3$ to $C_{12}$ cycloalkyloxy, $C_6$ to $C_{18}$aryloxy, $C_5$ to $C_{17}$heteroaryloxy, $C_3$ to $C_{12}$cycloalkylalkyloxy, $C_6$ to $C_{18}$aralkyloxy, $C_5$ to $C_{17}$heteroaralkyloxy, $C_1$ to $C_{18}$alkylthio, $C_3$ to $C_{12}$cycloalkylthio, $C_6$ to $C_{18}$arylthio, $C_5$ to $C_{17}$heteroarylthio, $C_3$ to $C_{12}$cycloalkylalkylthio, $C_6$ to $C_{18}$aralkylthio, $C_5$ to $C_{17}$heteroaralkylthio, $C_1$ to $C_{18}$alkyl-SO- or -SO$_2$, $C_3$ to $C_{12}$cycloalkyl-SO- or -SO$_2$, $C_6$ to $C_{18}$aryl-SO- or -SO$_2$, $C_5$ to $C_{17}$heteroaryl-SO- or -SO$_2$, $C_3$ to $C_{12}$cycloalkylalkyl-SO- or -SO$_2$, $C_6$ to $C_{18}$aralkyl-SO- or -SO$_2$, $C_5$ to $C_{17}$heteroaralkyl-SO- or -SO$_2$, tertiary amino with 3 to 30 carbon atoms, and alkoxyalkyl with 2 to 20 carbon atoms, with the proviso that two -NH$_2$ groups are not bond directly to different benzene rings and two OH groups are not directly bond to one ring of the benzo[4,5]imidazo[2,1-a]isoindol-11-one core structure.

The cyclic aliphatic and aromatic residues may be also substituted, with for example F, Cl or Br, -CN, -NO$_2$, $C_1$ to $C_{18}$alkyl, $C_3$ to $C_{12}$cycloalkyl, $C_6$ to $C_{18}$aryl, , $C_3$ to $C_{12}$cycloalkylalkyl, $C_6$ to $C_{18}$aralkyl, $C_5$ to $C_{17}$heteroaralkyl, $C_1$ to $C_{18}$alkyloxy, $C_3$ to $C_{12}$cycloalkyloxy, $C_6$ to $C_{18}$aryloxy. Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO-, methyl- or ethyl-SO$_2$-, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

Preferably 1 or 2 rings are condensed with the neighboring carbon atoms to form bicyclic or tricyclic systems. They may be selected from the group consisting of benzene, furane, thiophene, pyrrole, pyridine, and pyrimidine.

In a preferred embodiment, the bridging group corresponds to the formula XXV,

-X$_1$-(R$_1$)$_r$-(X$_2$)$_s$-R$_3$- (XXV), wherein

X$_1$, X$_2$, R$_1$, R$_3$, r and s have the meanings given before, inclusive of the preferred embodiments.

The functional groups A'$_1$ may be selected from the group consisting of alkyl bonded halogen like Cl and Br; -N$_3$, epoxide, -OH, -SH, -CN, -NHR$_{100}$, =C=NR$_{100}$, =CO, -CH-O, -NCO, -CH=CH$_2$, -C(CH$_3$)=CH$_2$, -C(O)OH, -SO$_3$H, -SO$_2$Cl, -SO$_2$Br, -C(O)-Cl, -C(O)-Br, -OC(O)-OR$_{101}$, -OC(O)-NR$_{102}$R$_{103}$, -C(O)-OR$_{104}$, -SO$_2$-OR$_{104}$, -C(O)-NR$_{102}$R$_{103}$, and -SO$_2$- NR$_{102}$R$_{103}$, wherein R$_{100}$ means H, $C_1$–$C_{18}$alkyl, phenyl, or benzyl, R$_{101}$ means $C_1$–$C_{18}$alkyl, phenyl, or benzyl, R$_{102}$ and R$_{103}$ independently from one another means H, $C_1$–$C_{18}$alkyl, phenyl, or benzyl, and R$_{104}$ means $C_1$–$C_{18}$alkyl, phenyl, or benzyl.

R$_{100}$, R$_{101}$, R$_{102}$, R$_{103}$ and R$_{104}$ contain as alkyl preferably 1 to 12, more preferably 1 to 8 and most preferably 1 to 4 carbon atoms.

More preferred functional groups A'$_1$ are selected from the group consisting of alkyl linked Cl and Br; epoxide, -OH, -SH, -NHR$_{100}$, -CH=CH$_2$, -C(CH$_3$)=CH$_2$, -NCO, -C(O)OH, -C(O)-Cl, -C(O)-Br, -C(O)-OR$_{104}$, -C(O)-NR$_{102}$R$_{103}$, wherein R$_{100}$ means H or $C_1$–$C_{12}$alkyl, R$_{102}$ and R$_{103}$ independently from one another means H or $C_1$–$C_4$alkyl, and R$_{104}$ means $C_1$–$C_8$alkyl.

In a mostly preferred embodiment the compounds correspond to formulae XXVI and XXVIa,

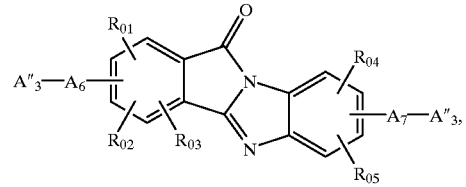

(XXVI)

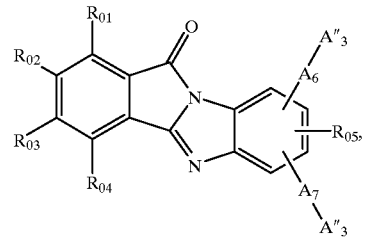

(XXVIa)

wherein

R$_{01}$, R$_{02}$, R$_{03}$, R$_{04}$, and R$_{05}$ independently from one another mean H, Cl, $C_1$ to $C_{18}$alkyl, $C_1$ to $C_{18}$alkoxy, phenyl, benzyl, $C_1$ to $C_{12}$ alkylphenyl or $C_1$ to $C_{12}$alkylbenzyl, A$_6$ and A$_7$ correspond to a bivalent residue of formula XXXIII, and A''$_3$ is selected from the group consisting of alkyl linked Cl and Br; epoxide, -OH, -SH, -NHR$_{100}$, -CH=CH$_2$, -C(CH$_3$)=CH$_2$, -NCO, -C(O)OH, -C(O)-Cl, -C(O)-Br, -C(O)-OR$_{104}$, -C(O)- NR$_{102}$R$_{103}$, wherein R$_{100}$ means H or $C_1$–$C_{12}$alkyl, R$_{102}$ and R$_{103}$ independently from one another means H or $C_1$–$C_4$alkyl, and R$_{104}$ means $C_1$–$C_8$alkyl, R$_{05}$ means preferably H.

In an especially preferred embodiment the bivalent groups A$_6$ and A$_7$ may be selected from the formulae -C(O)-O-R'-O-C(O)-(R'')$_u$- and -C(O)-NH-R'-NH-C(O)-(R'')$_u$-, wherein R' is $C_2$ to $C_{20}$, preferably $C_2$ to $C_{12}$, and more preferably $C_2$ to $C_6$alkylene, phenylene, benzylene, or oligoxyalkylene with preferably 2 to 6, and more preferably 2 to 4 oxyethylene and/or oxypropylene units, R" means $C_1$ to $C_{12}$alkylene, phenylene or benzylene, and u means 0 or 1, and groups -CH=$CH_2$ or -C($CH_3$)=$CH_2$ are linked to the C(O)-groups.

Especially preferred compounds correspond to the formula XXVII,

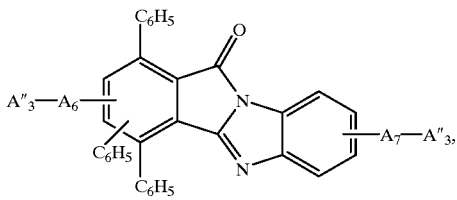

(XXVII)

wherein $A_6$ is $C_6H_4$ and $A_7$ is a direct bond or $C_1$ to $C_6$ alkylene, phenylene or benzylene, and A"$_3$ means -COOH, -C(O)-Cl, -C(O)-Br, -C(O)-$OR_{104}$, -C(O)- $NR_{102}R_{103}$, -C(O)O-$C_2$ to $C_{12}$ alkylene-OH, -C(O)O-$C_2$ to $C_{12}$ alkylene-O-C(O)-CH=$CH_2$, or -C(O)O-$C_2$ to $C_{12}$ alkylene-O-C(O)-C($CH_3$)=$CH_2$.

Monofunctional benzo[4,5]imidazo[2,1-a]isoindol-11-ones except amino, hydroxyl and carboxylphenyl substituted derivatives, and benzo[4,5]imidazo[2,1-a]isoindol-11-ones with one polyfunctional substituent are also novel, furthermore, in one aspect, and a further preferred embodiment of the invention, are compounds of formulae XXVIII and XXVIIIa, Chromophore-A"$_4$ (XXVIII), Chromophore-A"$_5$ (XXVIIIa), wherein A"$_4$ is a monovalent functional (also means polyrmerisable) group, which is linked directly or via a bridging group to the chromophore core structure, A"$_5$ is a di- or trifunctional (also means polymerisable) group, which is linked directly or via a bridging group to the chromophore core structure, and Chromophore is a monovalent benzo[4,5]imidazo[2,1-a]isoindol- 11-one, neighboring carbon atoms of the benzene rings of the chromophore can be condensed with benzene rings, heteroaromatic rings or both, and to these rings can be linked the free bond rather than to the benzene rings of the chromophore core structure, and the aromatic rings are unsubstituted or substituted with F, Cl or Br, -CN, -$NO_2$, $C_1$ to $C_{18}$alkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_1$ to $C_{18}$ aralkyl, $C_5$ to $C_{17}$heteroaralkyl, $C_1$ to $C_{18}$alkyloxy, $C_3$ to $C_{12}$ cycloalkyloxy, $C_6$ to $C_{18}$aryloxy, $C_5$ to $C_{17}$heteroaryloxy, $C_3$ to $C_{12}$cycloalkylalkyloxy, $C_1$ to $C_{18}$aralkyloxy, $C_5$ to $C_{17}$heteroaralkyloxy, $C_1$ to $C_{18}$alkylthio, $C_3$ to $C_{12}$cycloalkylthio, $C_6$ to $C_{18}$arylthio, $C_5$ to $C_{17}$heteroarylthio, $C_3$ to $C_{12}$cycloalkylalkylthio, $C_6$ to $C_{18}$aralkylthio, $C_5$ to $C_{17}$heteroaralkylthio, $C_1$ to $C_{18}$alkyl-SO- or -$SO_2$, $C_3$ to $C_{12}$cycloalkyl-SO- or -$SO_2$, $C_6$ to $C_{18}$aryl-SO- or -$SO_2$, $C_5$ to $C_{17}$heteroaryl-SO- or -$SO_2$, $C_3$ to $C_{12}$cycloalkylalkyl-SO- or -$SO_2$, $C_6$ to $C_{18}$aralkyl-SO- or -$SO_2$, $C_5$ to $C_{17}$heteroaralkyl-SO- or -$SO_2$, tertiary amino with 3 to 30 carbon atoms, and alkoxyalkyl with 2 to 20 carbon atoms, with the proviso, that in compounds of formula XXVIII, the group OH is linked via a bridging group, that the group -$NH_2$ is not bonded directly or via phenylene bridging group, and that the group COOH is not bonded via a phenylene bridging group to the benzene rings of the benzo[4,5]imidazo[2,1-a]isoindol-11-one core structure.

The cyclic aliphatic and aromatic residues (substituents) may be also substituted, with for example F, Cl or Br, -CN, -$NO_2$, $C_1$ to $C_{18}$alkyl, $C_3$ to $C_{12}$cycloalkyl, $C_6$ to $C_{18}$aryl, , $C_3$ to $C_{12}$cycloalkylalkyl, $C_6$ to $C_{18}$aralkyl, $C_5$ to $C_{17}$heteroaralkyl, $C_1$ to $C_{18}$alkyloxy, $C_3$ to $C_{12}$cycloalkyloxy, $C_6$ to $C_{18}$aryloxy.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO-, methyl- or ethyl-$SO_2$-, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

Preferably 1 or 2 rings are condensed with the neighboring carbon atoms to form bicyclic or tricyclic systems. They may be selected from the group consisting of benzene, furane, thiophene, pyrrole, pyridine, and pyrimidine.

In a preferred embodiment, the bridging group in compounds of formula XXVIII corresponds to the formula XXIX, -$X_1$-($R_1$)$_r$-($X_2$)$_s$-$R_3$- (XXIX), wherein $X_1$, $X_2$, $R_1$, $R_3$, r and s have the meanings given before, inclusive of the preferred embodiments.

The functional groups A"$_4$ and A"$_5$ may be selected from the group consisting of halogens like Cl and Br; -$N_3$, epoxide, -OH, -SH, -CN, -$NHR_{100}$, =C=$NR_{100}$, =CO, -CH=O, -NCO, -CH=$CH_2$, -C($CH_3$)=$CH_2$, -C(O)OH, -$SO_3$H, -$SO_2$Cl, -$SO_2$Br, -C(O)-Cl, -C(O)-Br, -OC(O)-$OR_{101}$, -OC(O)-$NR_{102}R_{103}$, -C(O)-$OR_{104}$, -$SO_2$-$OR_{104}$, -C(O)- $NR_{102}R_{103}$, and -$SO_2$- $NR_{102}R_{103}$, wherein $R_{100}$ means H, $C_1$–$C_{18}$alkyl, phenyl, or benzyl, $R_{101}$ means $C_1$–$C_{18}$alkyl, phenyl, or benzyl, $R_{102}$ and $R_{103}$ independently from one another means H, $C_1$–$C_{18}$alkyl, phenyl, or benzyl, and $R_{104}$ means $C_1$–$C_{18}$alkyl, phenyl, or benzyl.

$R_{100}$, $R_{101}$, $R_{102}$, $R_{103}$ and $R_{104}$ contain as alkyl preferably 1 to 12, more preferably 1 to 8 and most preferably 1 to 4 carbon atoms.

More preferred functional groups A"$_4$ and A"$_5$ are selected from the group consisting of alkyl linked Cl and Br; epoxide, -OH, -SH, -$NHR_{100}$, -CH=$CH_2$, -C($CH_3$)=$CH_2$, -NCO, -C(O)OH, -C(O)-Cl, -C(O)-Br, -C(O)-$OR_{104}$, -C(O)-$NR_{102}R_{103}$, wherein $R_{100}$ means H or $C_1$–$C_{12}$alkyl, $R_{102}$ and $R_{103}$ independently from one another means H or $C_1$–$C_4$alkyl, and $R_{104}$ means $C_1$–$C_8$alkyl.

In a mostly preferred embodiment the compounds of formula XXVIII correspond to formulae XXX and XXXa,

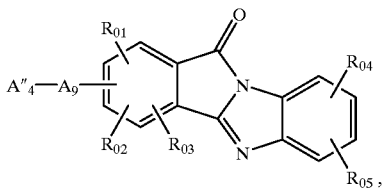

(XXX)

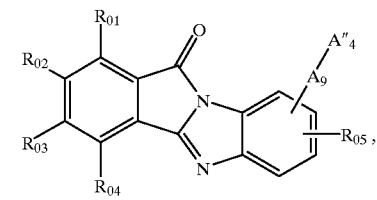

(XXXa)

wherein $R_{01}$, $R_{02}$, $R_{03}$, $R_{04}$, and $R_{05}$ independently from one another mean H, Cl, $C_1$ to $C_{18}$alkyl, $C_1$ to $C_{18}$alkoxy, phenyl, benzyl, $C_1$ to $C_{12}$ alkylphenyl or $C_1$ to $C_{12}$alkylbenzyl, $A_9$ is a direct bond or correspond to a bivalent residue of formula XXXIII, and $A''_4$ is selected from the group consisting of alkyl linked Cl and Br; epoxide, -OH, -SH, -NHR$_{100}$, -CH=CH$_2$, -C(CH$_3$)=CH$_2$, -NCO, -C(O)OH, -C(O)-Cl, -C(O)-Br, -C(O)-OR$_{104}$, -C(O)-NR$_{102}$R$_{103}$, wherein $R_{100}$ means H or $C_1$–$C_{12}$alkyl, $R_{102}$ and $R_{103}$ independently from one another means H or $C_1$–$C_4$alkyl, and $R_{104}$ means $C_1$–$C_8$alkyl. $R_{05}$ means preferably H.

In an especially preferred embodiment the bivalent group $A_9$ is a direct bond, $C_1$ to $C_{12}$ alkylene, phenylene, benzylene, $C_1$ to $C_{12}$ oxyalkylene, oxyphenylene, oxybenzylene, $C_1$ to $C_{12}$ thioalkylene, thiophenylene, thiobenzylene, or the bivalent group may be selected from the formulae -C(O)-O-R'-O-C(O)-(R")$_u$- and -C(O)-NH-R'-NH-C(O)-(R")$_u$-, wherein R' is $C_2$ to $C_{20}$, preferably $C_2$ to $C_{12}$, and more preferably $C_2$ to $C_6$alkylene, phenylene, benzylene, or oligoxyalkylene with preferably 2 to 6, and more preferably 2 to 4 oxyethylene and/or oxypropylene units, R" means $C_1$ to $C_{12}$alkylene, phenylene or benzylene, and u means 0 or 1, and groups -CH=CH$_2$ or -C(CH$_3$)=CH$_2$ are linked to the C(O)-groups.

Especially preferred compounds correspond to the formula XXVIII are

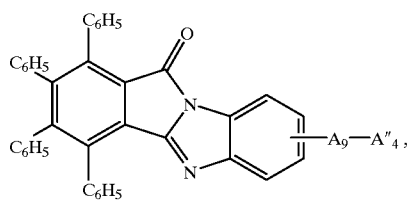

(XXXI)

wherein $A_9$ is a direct bond or $C_1$ to $C_6$ alkylene, phenylene or benzylene, and $A''_4$ means -COOH, -C(O)-Cl, -C(O)-Br, -C(O)-OR$_{104}$, -C(O)- NR$_{102}$R$_{103}$, -C(O)O-C$_2$ to C$_{12}$ alkylene-OH, -C(O)O-C$_2$ to C$_{12}$ alkylene-O-C(O)-CH=CH$_2$, or -C(O)O-C$_2$ to C$_{12}$ alkylene-O-C(O)-C(CH$_3$)=CH$_2$.

Examples of compounds of formula XXVIII are (Ph means phenyl):

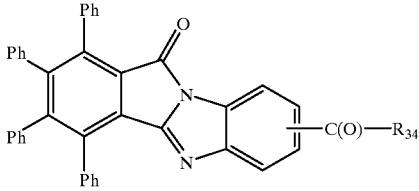

wherein $R_{34}$ is Cl, OH, OR$_{104}$ and R$_{104}$ means $C_1$–$C_8$alkyl, NR$_{102}$R$_{103}$ and R$_{102}$ and R$_{103}$ independently from one another mean H, $C_1$–$C_4$alkyl or $C_2$ to $C_4$ hydroxyalkyl, -C(O)O-C$_2$ to C$_{12}$ alkylene-O-C(O)-CH=CH$_2$, -C(O)O-C$_2$ to C$_{12}$ alkylene-O-C(O)-C(CH$_3$)=CH$_2$, -C(O)ONH-C$_2$ to C$_{12}$ alkylene-O-C(O)-CH=CH$_2$, or -C(O)NH-C$_2$ to C$_{12}$ alkylene-O-C(O)-C(CH$_3$)=CH$_2$;

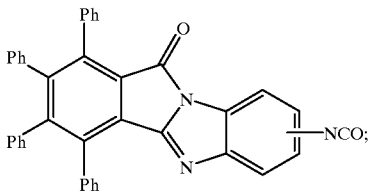

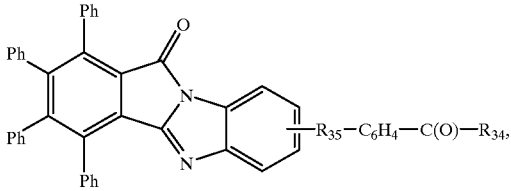

wherein $R_{35}$ is a direct bond, methylene, ethylidene, 2,2-propylidene, O, S, NH, N($C_1$ to $C_4$ alkyl), C(O) or C(O)NH, and $R_{34}$ has the meaning given before;

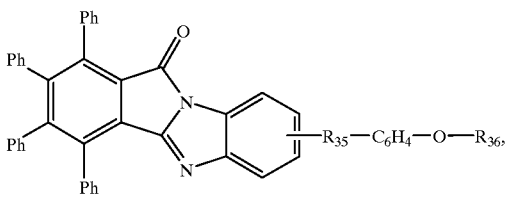

wherein $R_{35}$ has the meaning given before and $R_{36}$ means H, $C_2$ to $C_4$ hydroxyalkyl, glycidyl or OR$_{36}$ means NH-glycidyl or NHC$_2$ to $C_4$ hydroxyalkyl; and

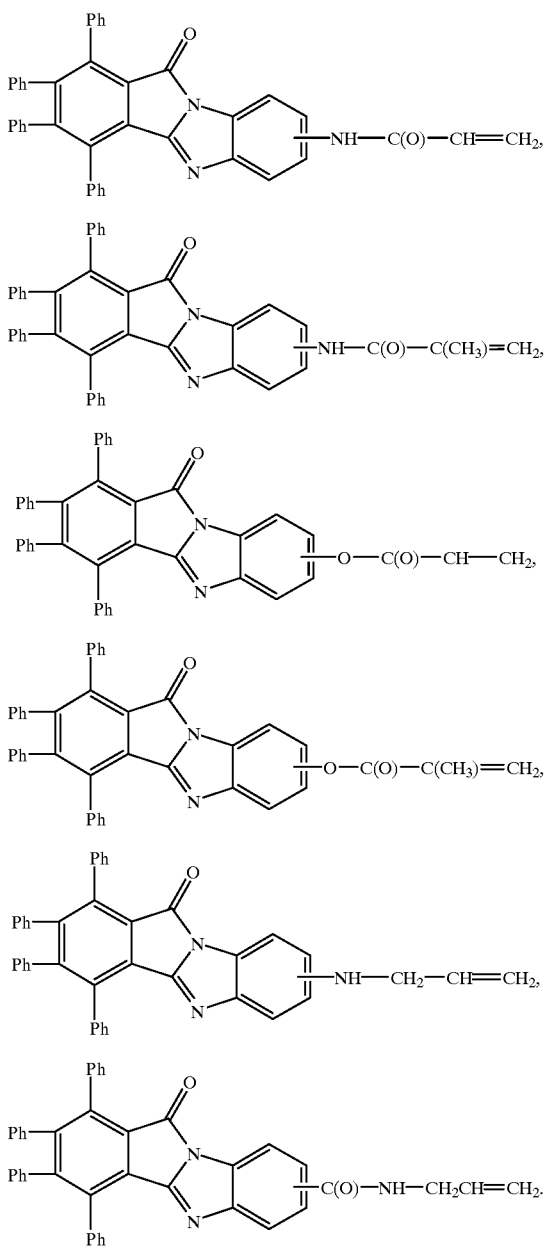

Preferred compounds of formula XXVIII correspond to the formulae XXXII and XXXIIa,

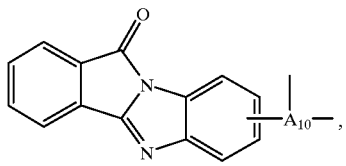
(XXXII)

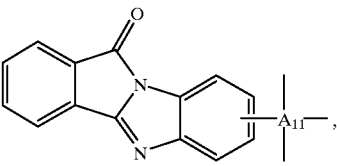
(XXXIIa)

wherein
neighboring carbon atoms of the benzene ring can be condensed with benzene rings, heteroaromatic rings or both, and the aromatic rings are unsubstituted or substituted with halogens like F, Cl or Br, -CN, -NO$_2$, C$_1$ to C$_{18}$ alkyl, C$_3$ to C$_{12}$ cycloalkyl, C$_6$ to C$_{18}$ aryl, C$_5$ to C$_{17}$ heteroaryl, C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$ aryloxy, C$_5$ to C$_{17}$ heteroaryloxy, C$_3$ to C$_{12}$ cycloalkylalkyloxy, C$_6$ to C$_{18}$ aralkyloxy, C$_5$ to C$_{17}$ heteroaralkyloxy, C$_1$ to C$_{18}$ alkylthio, C$_3$ to C$_{12}$ cycloalkylthio, C$_6$ to C$_{18}$ arylthio, C$_5$ to C$_{17}$ heteroarylthio, C$_3$ to C$_{12}$ cycloalkylalkylthio, C$_6$ to C$_{18}$ aralkylthio, C$_5$ to C$_{17}$ heteroaralkylthio, C$_1$ to C$_{18}$ alkyl-SO- or -SO$_2$, C$_3$ to C$_{12}$ cycloalkyl-SO- or -SO$_2$, C$_6$ to C$_{18}$ aryl-SO- or -SO$_2$, C$_5$ to C$_{17}$ heteroaryl-SO- or -SO$_2$, C$_3$ to C$_{12}$ cycloalkylalkyl-SO- or -SO$_2$, C$_6$ to C$_{18}$ aralkyl-SO- or -SO$_2$, C$_5$ to C$_{17}$ heteroaralkyl-SO- or -SO$_2$, tertiary amino with 3 to 30 carbon atoms, and alkoxyalkyl with 2 to 20 carbon atoms, the cyclic aliphatic and aromatic residues (substituents) may also be substituted, for example with halogens like F, Cl or Br; or -CN, -NO$_2$, C$_1$ to C$_{18}$ alkyl, C$_3$ to C$_{12}$cycloalkyl, C$_6$ to C$_{18}$ aryl, , C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$ aryloxy, and A$_{10}$ means a trivalent and A$_{11}$ means tetravalent organic group.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO-, methyl- or ethyl-SO$_2$-, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

Preferably the ring without the functional group is condensed with the neighboring carbon atoms to form bicyclic systems. They may be selected from benzene, furane, thiophene, pyrrole, pyridine, and pyrimidine.

In a preferred embodiment, A$_{10}$ corresponds to the formula XXXIII and A$_{11}$ corresponds to formula XXXIIIa,

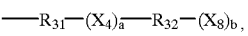
(XXXIII)

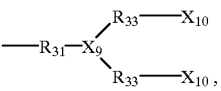
(XXXIIIa)

wherein
(a) R$_{31}$ is a direct bond, C$_1$ to C$_{12}$ alkylene, phenylene or benzylene;
X$_4$ is N, O, S, C(O)O or C(O)N;
R$_{32}$ means C$_2$ to C$_{12}$ alkyltriyl, phenyltriyl or benztriyl, when a is 1 and b is 2, or means C$_2$ to C$_{12}$ alkyltetrayl, phenyltetrayl or benztetrayl, when a is 1 and b is 3;

$X_8$ means OH, SH, $NH_2$, C(O)OH, $C(O)NH_2$, OC(O)-CH=$CH_2$, OC(O)-C($CH_3$)=$CH_2$, HNC(O)-CH-=$CH_2$, HNC(O)-C($CH_3$)=$CH_2$; or (b) $R_{32}$ is a bond, a is 0 and b is 2 or 3, $X_8$ has the above meanings and $R_{31}$ means $C_2$ to $C_{12}$ alkyltriyl, phenyltriyl or benztriyl, when b is 2, or means $C_2$ to $C_{12}$ alkyltetrayl, phenyltetrayl or benztetrayl, when b is 3;

(c) $R_{31}$ is a direct bond, $C_1$ to $C_{12}$ alkylene, phenylene or benzylene;

$X_9$ is N or C(O)N;

$R_{33}$ is $C_2$ to $C_{12}$ alkylene;

$X_{10}$ is OH, SH, C(O)OH, $C(O)NH_2$, or OC(O)-CH=$CH_2$, OC(O)-C($CH_3$)=$CH_2$, HNC(O)-CH=$CH_2$, HNC(O)-C($CH_3$)=$CH_2$ or -CH=$CH_2$.

$R_{31}$ and $R_{33}$ in the meaning of alkylene contain preferably 2 to 8 and mostly preferred 2 to 4 C-atoms. $R_{32}$ in the meaning of alktriyl contain preferably 2 to 8, more preferred 2 to 6, and mostly preferred 2 to 4 C-atoms.

In a preferred embodiment the polyfunctional compounds correspond to formulae XXXIV and XXXIVa,

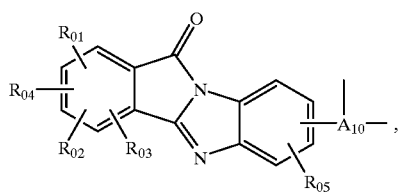

(XXXIV)

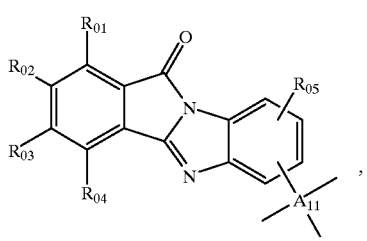

(XXXIVa), wherein $R_{01}$, $R_{02}$, $R_{03}$, $R_{04}$, and $R_{05}$ independently from one another mean H, Cl, $C_1$ to $C_{18}$ alkyl, $C_1$ to $C_{18}$ alkoxy, phenyl, benzyl, $C_1$ to $C_{12}$ alkylphenyl or $C_1$ to $C_{12}$ alkylbenzyl, $A_{10}$ correspond to formula XXXIII and $A_{11}$ corresponds to formula XXXIIIa. $R_{05}$ means preferably H.

In a preferred embodiment the group $A_{10}$ and $A_{11}$ may be selected from the group

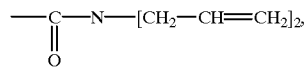

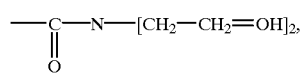

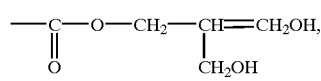

-continued

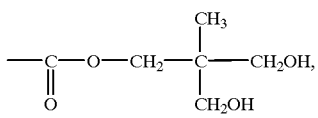

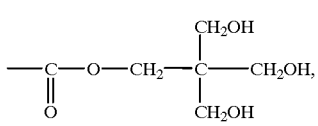

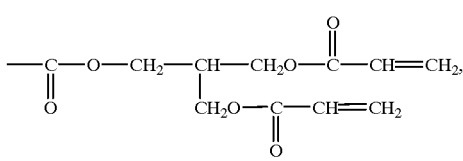

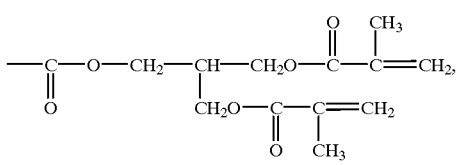

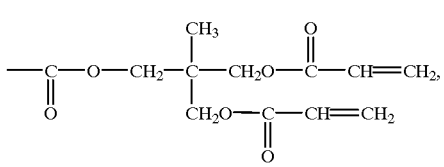

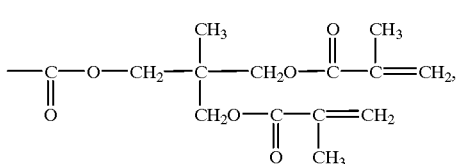

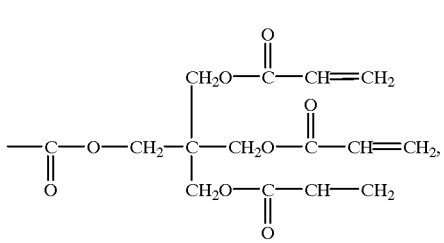

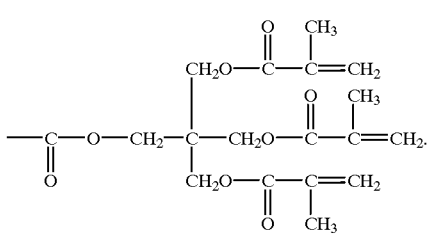

Some preferred examples of compounds of formulae XXXII and XXXIIa are compounds from the group (Ph means phenyl):

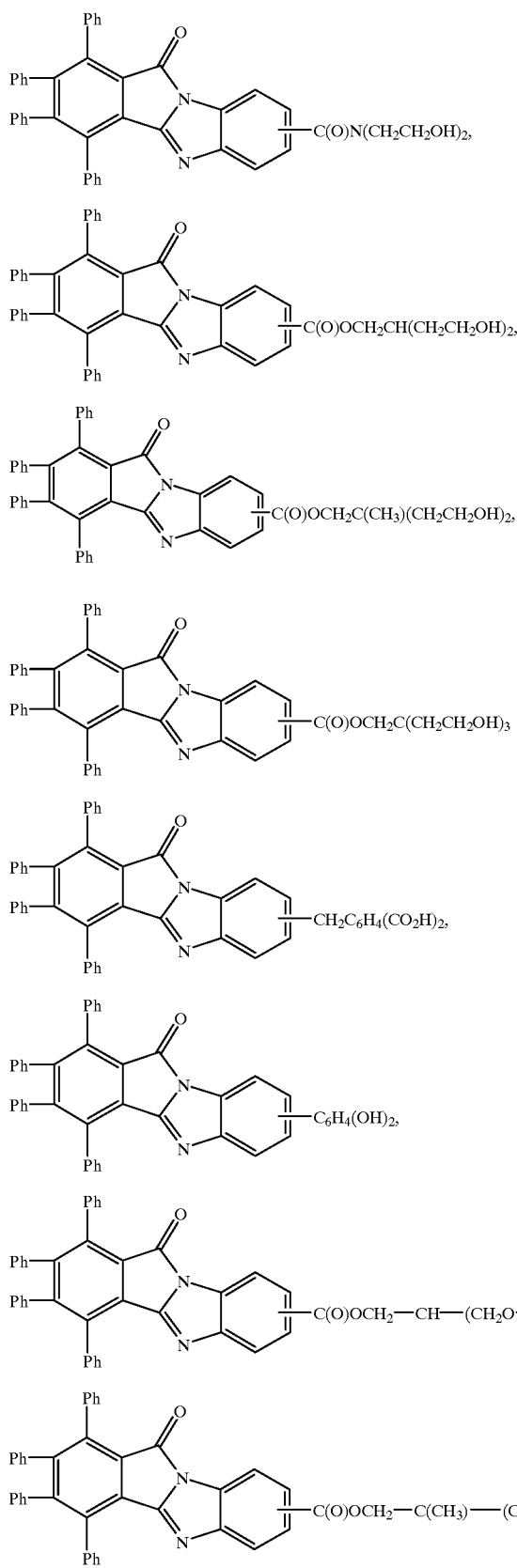
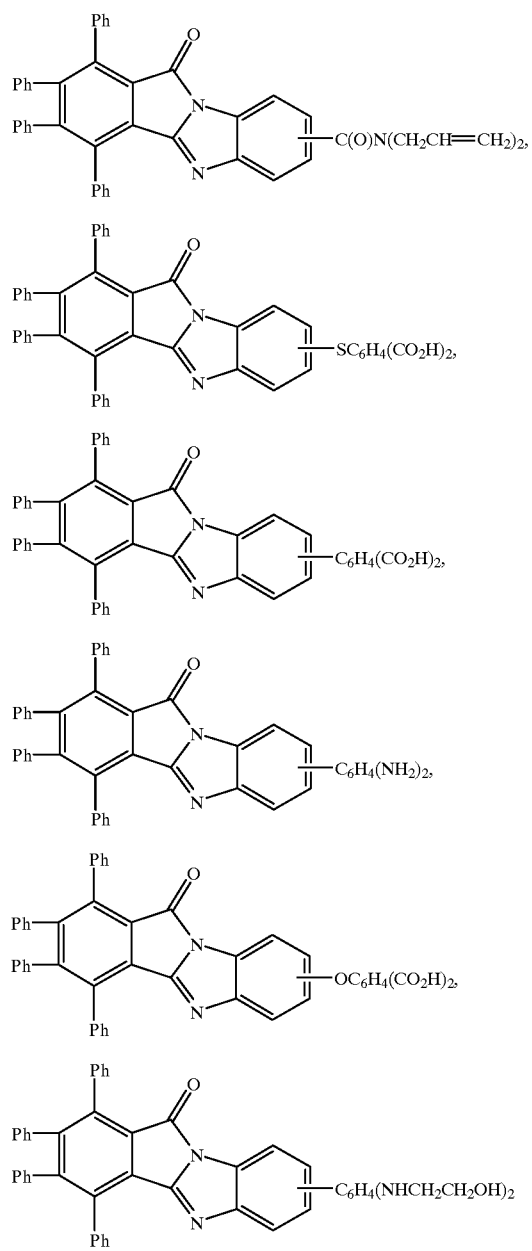

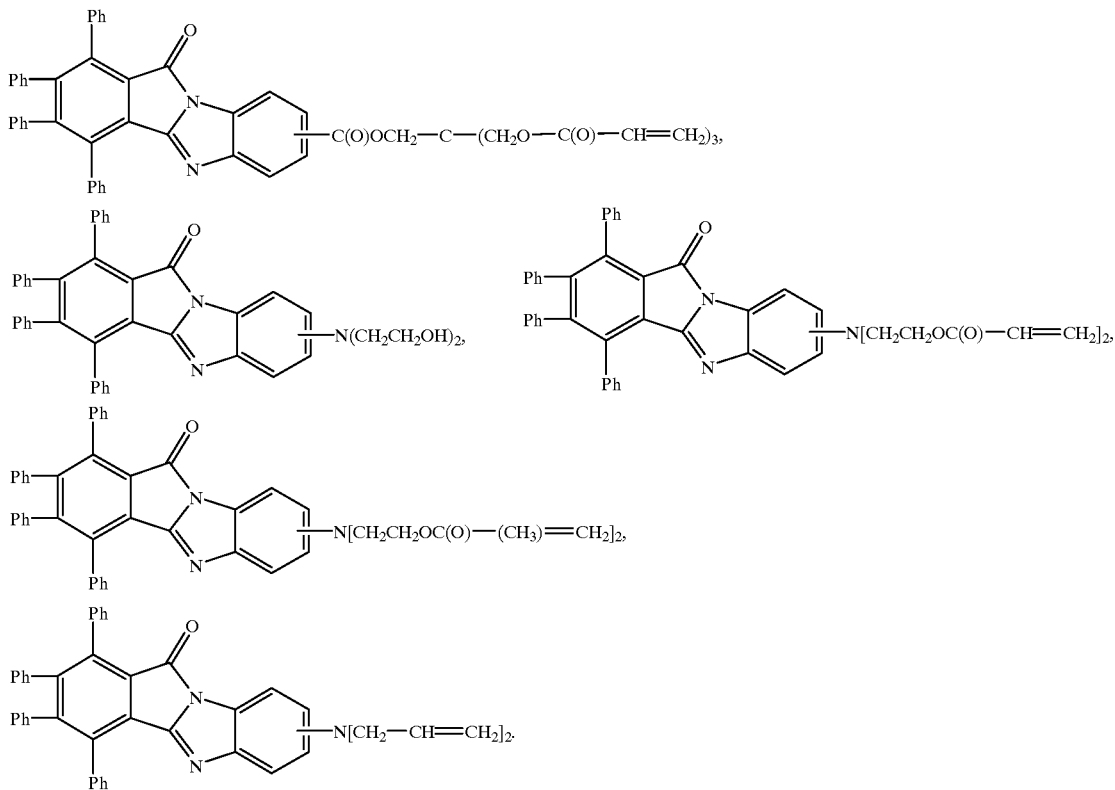

The chromophore monomers can be prepared according to the methods described in EP-A 0 456 609 wherein phthalic anhydrides are reacted with 1,2-diaminobenzenes, whereby the anhydride, the diaminobenzenes, or both, contain optionally protected functional groups.

As preferred examples for difunctional chromophores the following compounds may be mentioned:

pouring the completed reaction mixture slowly on ice which may contain an acid like HCl, yielding a precipitate, which may be filtered and dried, for example by vacuum pumping. This crude precipitate preferably may be further purified, to remove residual hydroxyethyl methacrylate, by re-precipitation for example from chloroform into a large excess of hexane.

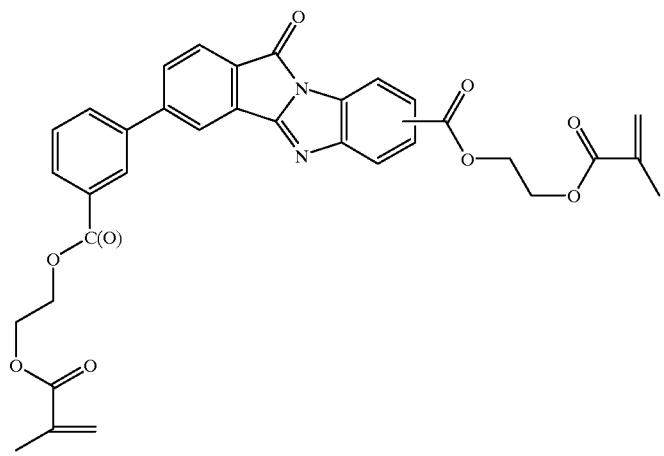

which may be synthesized starting from the corresponded acid chloride, for example by carrying out the reaction in a solvent like dry pyridine and thereby adding a, preferably large, excess of hydroxy ethyl methacrylate, preferably dissolved in the same solvent. Workup may be done by The corresponding acid chloride may be synthesized preferably reaction of the corresponding diacid compound with thionyl chloride, preferably in a solvent like dry benzene. The reaction mixture may be heated to complete the reaction, for example to reflux temperature. Solvent and excess thionyl chloride can be removed preferably using a stream of nitrogen.

The corresponding diacid compound may be synthesized for example starting from biphenyl-3,4,3' tricarboxylic acid, which is obtainable in accordance with the method described in Zh. Org. Khim 2(7), 1288 (1966), by reaction with 3,4-diamino benzoic, preferably in a solvent like acetic anhydride. The obtained benzo[4,5]-imidazo[2,1-a]isoindol-11-one-carboxylic diacid may be filtered and washed as usual with for example water and methanol, and may be further purified by column chromatography using preferably chloroform as the eluting solvent.

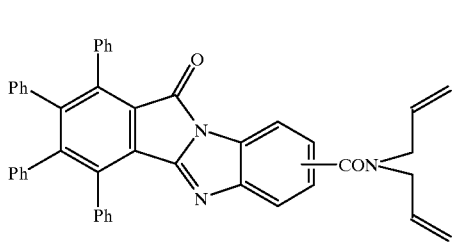

(II)

which may be synthesized starting from the corresponding tetraphenyl-benzo[4,5]-imidazo[2,1 -a]isoindol-11-one-carboxylic acid chloride (obtainable in a similar manner as the abovementioned diacid chloride) by reaction with diallylamine, preferably dissolved in a solvent like dry pyridine. Workup may be carried out by pouring the reaction mixture in ice cold water, washing the obtained crude reaction product with water and dried it. Further purification may be done via column chromatography using for example chloroform as the eluting solvent.

As an example for a preferable trifunctional chromophore the following compound may be manufactured:

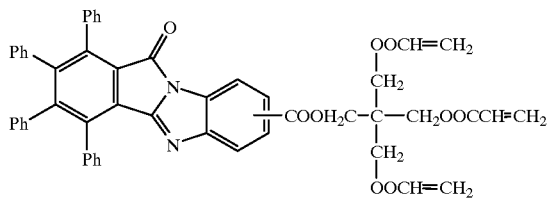

The preparation of this compound may be carried out starting from the corresponding trifunctional OH-derivative of tetraphenyl-benzo[4,5]imidazo[2,1-a]isoindol-11-one with acryloylchloride, preferably in a solvent like dichloromethane. Workup may be carried out in pouring the reaction mixture in a large excess of water, followed by filtering the obtained precipitate. If desired the crude product may be washed further for example with water and methanol and then dried, for example in an atmosphere under reduced pressure.

The corresponding trifunctional OH-derivative may be synthesized preferably by the reaction of pentaerythritol (large excess) with tetraphenyl-benzo[4,5]imidazo[2,1-a] isoindol-11-one-carboxylic acid chloride (obtainable by reaction of the corresponding carboxylic acid with thionyl chloride), preferably in a solvent like dry pyridine. Workup may be carried out as usual and described before.

The process to prepare the materials and compounds according to the invention may employ an inert solvent. Inert means, that the choice of a solvent is determined by the reactivity of the respective ingredients, hence a solvent preferably is selected such that no undesired side reactions occur. Solvents may also be employed in the actual application of the materials of the instant invention.

Suitable inert solvents are for example protic-polar and aprotic solvents, which may be used alone or in an admixture of at least two solvents. Examples are: water, alcohols (methanol, ethanol, propanol, butanol), ethyleneglycolmonomethyl- or -monoethylether, ether (bibutylether, tetrahydrofuran, dioxane, ethyleneglycol dimethylether, ethyleneglycoldiethylether, diethyleneglycoldiethylether, triethyleneglycoldimethylether), halogenated hydrocarbons (methylenchloride, chloroform, 1,2-dichloroethane, 1,1,1-trichlororethane, 1,1,2,2-tetrachloroethane), carboxylic esters and lactones (acetic acid ethylester, propionic acid methylester, benzoic acid ethylester, 2-methoxyethylacetate, γ-butyrolactone, δ-valerolactone, pivalolactone), carboxylic acid amides and lactames; N,N-dimethylformamide, N,N-diethylformamide, N,N-dimethylacetamide, tetramethylurea, hexamethylphosphorous acidtriamide, γ-butyrolactame, ε-caprolactame, N-methylpyrrolidone, N-acetylpyrrolidone, N-methylcaprolactame; sulfoxides (dimethylsulfoxide), sulfones (dimethylsulfone, diethylsulfone, trimethylenesulfone, tetramethylenesulfone), tertiary amines (N-methylpiperidine, N-methylmorpholine), aliphatic and aromatic hydrocarbons like petroleumether, pentane, hexane, cyclohexane, methylcyclohexane, benzene or substituted benzenes (chlorobenzol, o-dichlorobenzene, 1,2,4-trichlorobenzene, nitrobenzene, toluole, xylole) and nitriles (acetonitrile, propionitrile, bezenentrile, phenylacetonitrile).

The compound 1,2,3,4-tetraphenyl-benzo[4,5]imidazo [2,1 -a]isoindol-11-one and its derivatives, which are a preferred group of fluorescent compounds of this invention, possess an absorption maximum at around 370 nm, which lies in the UV region. However, their excitation wavelengths stretch from around 350 nm, in the UV, to 450 nm, in the visible region of the electromagnetic spectrum. Consequently, materials employing this class of compound, can span a broad number of applications as they readily facilitate themselves to excitation by both UV and daylight radiation sources. Correspondingly these materials can be rendered very useful as coloring agents in applications such as road markings and traffic signs for night and daylight uses, as they exhibit brilliant daylight fluorescence and can also be excited by the UV radiation of motor vehicles halogen lamps, thereby providing intense, bright colors during both day and nighttime. Other applications include their use as pigments, coloring agents, materials for scintillators, materials for solar energy collectors, materials for light emitting electroluminescent devices, materials for generating fluorescent images as well as in printing inks. It is also possible to produce fluorescent images (high relief structures) by the well known photoresist technology.

The compositions according to the invention may be used in various forms depending upon the end-use purpose:

The polymers of completion form (A) may be milled or can be produced in the form of particles. A further preferred embodiment of the invention is a polymer according to the completion form (A) in the form of particles, especially finely divided particles.

The average diameter or particle size may correspond to that of the particles according to completion form (B). The polymers according to the invention may be admixed with other polymers. A further preferred embodiment of the invention is a composition containing (a) a polymer substrate and (b) in a, preferably uniform, distribution a polymer according to the completion form (A).

The amount of component (b) may be for example from 0.1 to 99.9 percent by weight, preferably 1.0 to 50 with respect to the total composition. The amount used depends essentially from the amount of chromophore structural units on the polymer of completion form (A) and on compatibility with the polymer substrate.

The polymers may be selected from thermoplastics, thermosettings and structurally crosslinked polymers. The admixture of thermoplastics with thermoplastics of completion form (A) are polymeric alloys. The polymers may be homopolymers, copolymers, blockpolymers, graft polymers or random polymers.

The polymers may be opaque or translucent, but preferably transparent. The polymers may be selected for example from the group of thermoplastic polymers like polyesters, polyamides, polyimides, polyamide-imides, polyamide esters, polyurethanes, polyureas, polyolefines; polymers from substituted olefines like vinylethers, vinylesters, vinylalcohols, vinylchloride, vinyldichloride, acetonitrile, acrylic acid, methacrylic acid, esters and amides of acrylic acid and methacrylic acid, styrene, chlorostyrene, methylstyrene, styrene sulfonic acid and their esters and amides, vinylcarbazole, vinylpyridine, vinylpyrrolidone: polymaleic acid and esters and amides therefrom; polyethers, polysufones, polyketones, polyphenylsulfides, and polyacetales; cellulose and its esters and ethers, and starch or derivatives of starch.

Examples of thermosetting resins and structurally crosslinked resins are polyepoxides, unsaturated polyesters, photocrosslinked resins for example from acrylic acid and/or methacrylic esters and/or amides from polyols and/or polyamines, melamine/formaldehyde resins, and phenol/formaldehyde resins; polymers from butadiene, isoprene and or chloroprene and copolymers with olefins, which may be crosslinked and of rubbery nature; as well as silicates obtainable for example through the known sol/gel process.

The thermoplastic compositions can be obtained by known mixing methods such as admixing solutions of polymers and removing the solvent, injection molding and extrusion molding. Thermosetting and structurally crosslinked compositions are obtainable by known methods like press molding, whereby the polymer of completion form (A) is preferably low molecular weight and dissolved in the polymerisable mixture.

In a further aspect of the invention polymer particles of completion form (B) or completion form (A) or both together may be used as filler for thermoplastic, thermosetting and structurally crosslinked polymers.

A further preferred embodiment of this invention is a composition comprising (a) a polymer substrate, and (b) particles of the completion form (B), polymer particles of a polymer according to the completion form (A) or both uniformly distributed therein.

The amount of the particles may for example be 0.01 to 90 wt- %, preferably 0.1 to 90 wt- %, and more preferably 1 to 50 wt- % of the total composition.

The polymer substrate may include those as described above. This composition can be easily prepared by known mixing methods as described above, whereby the particles are dispersed prior to the polymerization of a precursor composition.

The polymeric compositions of the invention may contain further ingredients to enhance certain features such as electrical, physical and mechanical properties, and/or the processability, for example dispersing agents to achieve a uniform distribution of particles, lubricants, plasticizers, antistatica, solvents, molding agents, antioxidants, light stabilizers, fillers and reinforcing fillers like glass balls and glass fibbers, silicates (mica, clay, wollastonite), metal and semiconductor metal oxides, metal carbonates, metal salts, metals and semiconductor metals, carbon black, as powder, or carbon fibers, whiskers, metal and semiconductor metal carbides, metal and semiconductor metal nitrides, dyes, pigments and others.

The compositions of the invention me be used in the form of shaped articles, including the surface modified compositions of completion form (B).

A further preferred embodiment of the invention is therefore a shaped article from (a) the composition according to the polymers of completion form (A), or (b) a composition of (b1) a polymer substrate containing either (b2) polymers according to the completion form (A), or (b3) particles of the polymers of completion form (A), of completion form (B) or both, alone or together with a polymer of the completion form (A), uniformly distributed in the polymer substrate.

In another aspect the polymers and particles of the completion form (A) or the particles of the completion form (B) may be used as coatings on carrier materials, using the above mentioned compositions.

Another preferred embodiment of the invention is a composition comprising (a) a carrier material and (b) at least on one surface a coating of (1) a polymer of completion form (A), (2) a polymer substrate containing uniformly distributed particles of the completion form (A), completion form (B) or both, or (3) a polymer mixture comprising a substrate polymer and in uniform distribution a soluble polymer of completion form (A) and in admixture particles of the completion form (A), completion form (B) or both.

Suitable carrier materials may be selected from organic or inorganic materials like glass, ceramics, minerals, plastics, paper, wood, semiconductors, metals, metal oxides and semiconductor metal oxides, and metal or semiconductor metalnitrides or -carbides.

The thickness of the coating depends on the desired end-use and may be from 0.1 to 1000 $\mu$m, preferably 0.5 to 500 $\mu$m, and especially preferred 1 to 100 $\mu$m.

The coatings may be protected by covering coatings which are preferably transparent. Such coatings are well known, and in general photocrosslinked coatings are mainly used for this purpose. Moreover, the materials belonging to completion form (A), which are surface modified, may also be protected by coatings.

The coated materials are obtainable by known methods like painting, casting or spincoating, directly or with a solution or dispersion of the polymeric compositions. It is also possible to use a polymerisable composition containing polymer forming monomers, especially crosslinkable olefinically unsaturated monomers. The polymerization may be induced thermally or by actinic radiation. The coating compositions are novel and a further preferred embodiment of the invention.

A further preferred embodiment of the invention is therefore a liquid and a solvent containing composition, comprising;

(1) a polymer of completion form (A), and optionally a nonfluorescent polymer, (2) a polymer substrate containing uniformly dispersed particles of the completion form (A), (B) or both, alone or in admixture with a soluble polymer of completion form (A).

These compositions may contain a solvent, such as those mentioned before, and optionally surfactants and dispersing agents. The viscosity range depends on the final application for the coating wherein the desired viscosity can be achieved by choice and quantity of solvent, polymers as binders and fluorescent materials. To further achieve a desired viscosity, thickening agents may additionally be used. Again suitable solvents have been mentioned.

The preparation of this composition can be achieved by simply mixing the ingredients together using suitable mixing equipment Dispersions are in general stable depending upon the viscosity. If particles should aggregate they may be redistributed by stirring.

In a highly advantageous embodiment of preparing coatings, polymerisable compositions can be used, wherein a t least one surface of a carrier material is coated and subsequently polymerized by heat or radiation. Photopolymerizable mixtures can also be used to generate fluorescent images by known photoresist technology.

A further preferred embodiment of the invention is a polymerisable composition comprising a) polymerisable monomers or prepolymers in admixture With particles of completion forms (A), (B) or both, and optionally dissolved therein a polymer according to completion for m (A);

b) polymerisable monomers or prepolymers and dissolved therein a polymer according to completion form (A); or c) a polymerisable chromophore structure, which contains at least one polymerisable group or at least two functional groups or a prepolymer of it, and optionally nonfluorescent monomers or prepolymers copolymerisable with both that of the fluorescent chromophore monomer.

The composition may be used to generate the polymers of completion form (A) as described before. Preferably the composition contains a solvent. The afore described embodiments also apply to this composition, inclusive of preferred embodiments.

In a preferred embodiment the composition is based on polymerisable monomers and/or prepolymers containing a group selected from olefinically unsaturated groups, preferably from -CH=$CH_2$ and -C($CH_3$)=$CH_2$, which can be thermally and/or photo-polymerized.

Photopolymerisable monomers and prepolymers are well known in the art and for example are described in EP-A-0 654 711. Preferred photopolymerisable monomers and prepolymers are those based on the esters or amides of acrylic acid or methacrylic acid and alcohols, polyols, amines and polyamines.

The photopolymerisable composition is particularly suitable to generate coatings and images.

A further preferred embodiment of the invention is a composition comprising (a) a carrier material and on at least one surface of the carrier is (b) a high relief image of a polymerized photoresist material, which contains (b1) particles of completion forms (A), (B) or both in uniform distribution, and optionally dissolved therein a polymer according to completion form (A);

(b2) uniformly distributed therein a polymer according to completion form (B); or (b3) a polymer from a photopolymerisable chromophore containing at least one polymerisable group or at least two functional photoreactive groups or a prepolymer of it, and optionally non-fluorescent monomers or prepolymers copolymerisable by irradiation with that of the chromophore containing monomer.

A further preferred embodiment of the invention is a process for the preparation of fluorescent high relief images on a carrier. This involves irradiating under a mask or by laser writing, the above coated photopolymerisable composition (which has been dried and removed of solvent) on the carrier, developing the irradiated composition and finally removing the non-irradiated parts.

Removal of the non-irradiated parts is mostly carried out by treatment with solvent.

All the materials described before are highly fluorescent materials and can broadly be used in optical and electroptical devices.

A further preferred embodiment of the invention is a process for the creation of fluorescent radiation which requires exciting, electrically or by UV/visible radiation, or both, a fluorescent composition of the instant invention.

Another preferred embodiment of the invention is the use of the compositions according to the invention as fluorescent materials.

The compound 1,2,3,4-tetraphenyl-benzo[4,5]imidazo[2, 1-a]isoindol-11-one and its derivatives, which are representative of the class of chromophore compounds used in this invention, in general possess an absorption maximum at around 370 nm, which lies in the UV region. However, their excitation wavelengths usually stretch from around 350 nm, in the UV, to 450 nm, in the visible region of the electromagnetic spectrum. Consequently, these polymeric materials can span a broad number of applications as they readily facilitate themselves to excitation by both UV and daylight radiation sources. Therefore, these materials could be rendered very useful as coloring agents in applications such as road markings and traffic signs, as they exhibit brilliant daylight fluorescence and can also be excited by the UV radiation of a motor vehicles halogen lamp, thereby providing intense, bright colors during both day and nighttime. Other applications include their use as pigments, coloring agents, materials for scintillators, materials for solar energy collectors, materials for light emitting electroluminescent devices or materials for generating fluorescent images etc.

The composition of the present invention emits solid state fluorescence with a high emission intensity according to observations hitherto.

The following examples demonstrate the invention.

A) Preparation of Mono-vinyl Fluorescent Compound (A3) and its Intermediates (A1, A2).

EXAMPLE A1

1,2,3,4 tetraphenyl- benzo[4,5]imidazo[2,1 -a] isoindol-11-one-7-carboxylic acid (A1, inclusive the corresponding 8-isomer)

Into a reaction vessel equipped with a condenser, light nitrogen purge and magnetic stirrer, 10 g (0.022 mol) of tetraphenylphthalic anhydride and 3.35 g (0.022 mol) of 3,4 diaminobenzoic acid are added, along with 100 ml of acetic acid. The gray colored reaction mixture is heated to reflux temperature. After several hours the reaction begins to take-on a dark yellow color. The reaction mixture is then left for a further 72 hours at slightly below reflux temperature (105° C.).

The bright yellow precipitate is filtered and washed with water and methanol. The yellow product is then left to dry at the water pump vacuum before final drying in a vacuum oven overnight (60° C.). The obtained yield is 81%.

EXAMPLE A2

1,2,3,4 tetraphenyl-benzo[4,5]imidazo[2,1-a] isoindol-11-ones-7(or 8) carboxylic acid chloride (A2, inclusive the corresponding 8-isomer)

Into a reaction vessel equipped with a condenser, light nitrogen purge and magnetic stirrer, 5 g (0.0088 mol) of compound A1 and 30 ml of dry benzene are added. Keeping at room temperature, a molar excess of thionyl chloride is added to the reaction mixture, which is then allowed to stir for 30 minutes. The reaction mixture, which is a yellow suspension, is then heated to reflux temperature for about 2 hours, to yield a clear golden colored solution. The solvent and excess thionyl chloride are removed using a stream of nitrogen, to furnish the yellow acid chloride derivative. The yield is 94%.

EXAMPLE A3

1,2,3,4 tetraphenyl-11H-benzo[4,5]imidazo[2,1 -a] isoindol-11-ones-7-carboxy ethyl methacrylate (B1, inclusive the corresponding 8-isomer)

4 g of A-2, dissolved in 30 ml of dry pyridine are added slowly over the period of about 30 minutes, to a stirred solution containing 5 g (large excess) hydroxy ethyl methacrylate in 10 ml of dry pyridine at room temperature. The reaction mixture is left at room temperature to stir for a further 2 hours.

The completed reaction mixture is then slowly added, with stirring, to a beaker containing 100 g of ice and 100 ml of 1 M HCl. A yellow precipitate is obtained and allowed to settle before filtration (sinter glass G3), by vacuum pumping, to yield the crude product. The crude precipitate is further purified, to remove residual hydroxyethyl methacrylate, by re-precipitation from chloroform into a large excess of hexane (Yield 86%).

B) Preparation of Linear Copolymer containing a Fluorescent Chromophore 2.04 g of solid-state fluorescent monomer A3, 1.7 g of freshly distilled methyl methacrylate, 0.0172 g of recrystallized AIBN (α,α'-azo-bisisobutyronitrile) and 12 ml of are added to a clean reaction flask. The reaction feed mixture is degassed by bubbling dry nitrogen gas through the mixture for 30 min and placed in a temperature controlled water bath at 60° C. for 8 hours. The viscous solution is slowly poured into a large excess of methanol or hexane, where upon the a yellow precipitate is afforded. The polymer is purified by a further two reprecipitation. (Yield 53%, Mw $2.5 \times 10^5$ gmol$^{-1}$).

C) Preparation of a Solid-State Fluorescent Crosslinked Composition 0.2337 g of A3, 0.5295 g of ethylene glycol dimethacrylate (EGDM) and 0.2396 g, hydroxy ethyl methacrylate (HEMA), 0.0078 g of azobisisobutyronitrile (AIBN) and 1.5 ml of chloroform is removed of oxygen by bubbling nitrogen through the feed mixture. Whist maintaining a nitrogen atmosphere the monomer solution is added to 15 ml of vigorously stirred water. The water is itself removed of oxygen by bubbling with nitrogen for a period of 30 minutes. After a period of about 2 hours a mass of solid, insoluble crosslinked particles is furnished. Theses particles are filtered and washed several times in chloroform or DMF solution to remove all unreacted monomers. The afforded particles display intense solid-state fluorescence. (Yield 86%).

Application Examples

Photoluminescence and excitation spectra of all fluorescent polymer samples are recorded using a Hitachi F-4500 Fluorescence Spectrophotometer in the standard reflectance mode, with the aid of a commercial solid sampler that possesses a transparent quartz window. All polymer samples are ground into fine powders, via a standard laboratory mortar and pestle, and uniformly packed into the sample holder. The monochromatic excitation wavelength is 365 nm and the scan rate 240 nm/min. The measured emission wavelength for various polymeric systems are detailed in Table 1.

TABLE 1

| Example | Chromophore | Comonomers | | Emission Maximum | Intensity (arb. units) |
|---|---|---|---|---|---|
| B | A3 (54 wt %) | MMA (46 wt %) | | 498 nm | 1001 |
| C | A3 (23 wt %) | EGDM (53 wt %) | HEMA (24 wt %) | 494 nm | 1120 |

We claim:

1. A composition comprising a solid organic support material to which are either directly, or via a bridging group, covalently linked fluorescent chromophores, characterized in that the chromophores are selected from the group consisting of benzo[4,5]imidazo[2,1-a]isoindol-11-ones.

2. A composition according to claim 1, characterized in that the support material is selected from the group consisting of linear or crosslinked polymers with pendent chromophores, and surface modified polymers containing pendent chromophores on their surfaces.

3. A composition according to claim 2, characterized in that it comprises a completion form (A) consisting essentially of polymers with chromophore molecules, which are either directly, or via a bridging group, covalently linked to the backbones of the polymers.

4. A composition according to claim 2, characterized in that it comprises a completion form (B) consisting essentially of organic support materials to which chromophore molecules are either directly or via a bridging group covalently linked to the surfaces of said support materials.

5. A process for the manufacture of a composition according to claim 3, which comprises reacting a compound of the formula XVIII, XIX and/or XXIII in any chromophore combination, alone or together with comonomers, $A'_1$—Chromophore (XVIII)

$A'_2$—chromophore—$A'_2$ (XIX)

Chromophore-$(A'_3)_c$ (XXIII)

wherein $A'_1$ is a monovalent functional or polymerisable group, $A'_2$ is a monovalent functional or polymerisable group coreactive with $A'_1$, $A'_3$ is a monovalent functional or polymerisable group coreactive with functional or polymerisable groups on the polymer and c is 2 or 3, and Chromophore is a compound selected from the group consisting of tetraphenyl derivatives of benzo[4,5] imidazo[2,1-a]isoindol-11-ones, whereby the $A'_1$, $A'_2$ and $A'_3$ are linked directly or via a bridging group to the chromophore body.

6. A process for the manufacture of a composition according to claim 3, which comprises reacting a polymer with recurring structural elements containing, either directly or through a bridging group, covalently linked functional or polymerisable groups, with a compound of the formula XVIII, XIX and/or XXIII in any chromophore combination, alone or together with comonomers, $A'_1$—Chromophore (XVIII)

$A'_2$—chromophore—$A'_2$ (XIX)

$$\text{Chromophore-}(A'_3)_c \quad \text{(XXIII)}$$

wherein $A'_1$ is a monovalent functional or polymerisable group, $A'_2$ is a monovalent functional or polymerisable group coreactive with functional or polymerisable groups of the polymer, $A'_3$ is a monovalent functional or polymerisable group coreactive with functional or polymerisable groups on the polymer and c is 2 or 3, and Chromophore is a compound selected from the group consisting of tetraphenyl derivatives of benzo[4,5]imidazo[2,1-a]isoindol-11-ones, whereby the $A'_1$, $A'_2$ and $A'_3$ are linked directly, or via a bridging group, to the chromophore body.

7. A composition, characterized in that it represents (a) a polymer substrate and (b) in an distribution therein a polymer of a completion form (A) consisting essentially of polymers with chromophore molecules exhibiting solid state fluorescence, which are either directly, or via a bridging group, covalently linked to the backbones of the polymers.

8. A composition, characterized in that it comprises (a) a polymer substrate, and (b) particles of a completion form (B) consisting essentially of organic support materials to which chromophore molecules are either directly or via a bridging group covalently linked to the surfaces of said support materials, or polymer particles of a polymer according to a completion form (A) consisting essentially of polymers with chromophore molecules, which are either directly, or via a bridging group, covalently linked to the backbones of the polymers or both uniformly distributed therein.

9. A composition comprising (a) a carrier material and (b) at least on one surface a coating of
   (1) a polymer of a completion form (A) consisting essentially of polymers with chromophore molecules, which are either directly, or via a bridging group, covalently linked to the backbones of the polymers,
   (2) a polymer substrate containing uniformly distributed particles of the completion form (A), a completion form (B) consisting essentially of organic support materials to which chromophore molecules are either directly or via a bridging group covalently linked to the surfaces of said support materials or both, or
   (3) a polymer mixture comprising a substrate polymer and in uniform distribution a soluble polymer of completion form (A) and in admixture particles of the completion form (A), completion form (B) or both.

10. A polymerisable composition comprising
   a) polymerisable monomers or prepolymers in admixture with particles of a completion form (A) consisting essentially of polymers with chromophore molecules, which are either directly, or via a bridging group, covalently linked to the backbones of the polymers, a completion form (B) consisting essentially of organic support materials to which chromophore molecules are either directly or via a bridging group covalently linked to the surfaces of said support materials or both, and optionally dissolved therein a polymer according to completion form (A);
   b) polymerisable monomers or prepolymers and dissolved therein a polymer according to completion form (A); or
   c) a polymerisable chromophore containing at least one polymerisable group or at least two functional groups or a prepolymer of it, and optionally nonfluorescent comonomers or prepolymers copolymerisable with that of the chromophore monomer compound.

11. A composition comprising (a) a carrier material and on at least one surface of the carrier there is
   (b) a high relief image of a polymerized photoresist material, which contains
   (b1) particles of a completion form (A) consisting essentially of polymers with chromophore molecules, which are either directly, or via a bridging group, covalently linked to the backbones of the polymers, a completion form (B) consisting essentially of organic support materials to which chromophore molecules are either directly or via a bridging group covalently linked to the surfaces of said support materials or both in uniform distribution; and optionally dissolved therein a polymer according to completion form (A);
   (b2) uniformly distributed therein a polymer according to completion form (B); or
   (b3) which is a polymer from a photopolymerisable chromophore containing at least one polymerisable group or at least two functional photoreactive groups or a prepolymer of it, from a chromophore containing at least one photopolymerisable group or at least two photoreactive functional groups or a prepolymer of it copolymerisable with that of the chromophore compound, and optionally monomers or prepolymers copolymerisable by irradiation with that of the chromophore.

12. A process for the preparation of fluorescent high relief images on a carrier, which comprises irradiating, under a mask or by laser writing, the dry coated photopolymerisable composition according to claim 11 on the carrier, developing the irradiated composition and finally removing the non-irradiated parts.

* * * * *